US011760994B2

(12) United States Patent
Bacigalupo et al.

(10) Patent No.: US 11,760,994 B2
(45) Date of Patent: Sep. 19, 2023

(54) SEPARATING POLYNUCLEOTIDE FRAGMENTS

(71) Applicants: ILLUMINA, INC., San Diego, CA (US); ILLUMINA CAMBRIDGE LIMITED, Cambridge (GB)

(72) Inventors: Maria Candelaria Rogert Bacigalupo, Encinitas, CA (US); Frank Steemers, Encinitas, CA (US); Jeffrey Fisher, San Diego, CA (US); Andrew Slatter, Cambridge (GB); Lewis Kraft, San Diego, CA (US); Niall Gormley, Cambridge (GB); M. Shane Bowen, Encinitas, CA (US)

(73) Assignees: ILLUMINA, INC., San Diego, CA (US); ILLUMINA CAMBRIDGE LIMITED, Cambridge (GB)

( * ) Notice: Subject to any disclaimer, the term of this patent is extended or adjusted under 35 U.S.C. 154(b) by 18 days.

(21) Appl. No.: 17/358,892

(22) Filed: Jun. 25, 2021

(65) Prior Publication Data

US 2022/0002711 A1 Jan. 6, 2022

Related U.S. Application Data

(60) Provisional application No. 63/048,347, filed on Jul. 6, 2020.

(51) Int. Cl.
*C12N 15/10* (2006.01)
(52) U.S. Cl.
CPC ..... *C12N 15/1065* (2013.01); *C12N 15/1093* (2013.01)

(58) Field of Classification Search
CPC .................................................. C12N 15/1065
(Continued)

(56) References Cited

U.S. PATENT DOCUMENTS

| 8,709,717 B2* | 4/2014 | Gunderson | C12N 15/101 435/177 |
| 2015/0284714 A1* | 10/2015 | Gormley | C12Q 1/6874 506/26 |
| 2017/0204457 A1* | 7/2017 | Crawford | C12Q 1/6869 |

OTHER PUBLICATIONS

Koota et al. Reversible, meniscus-free molecular combing of long-chain DNA. Langmuir, 2007, 23, 9365-9368. (Year: 2007).*

(Continued)

*Primary Examiner* — Aaron A Priest
*Assistant Examiner* — Randi Lynn Beil
(74) *Attorney, Agent, or Firm* — HESLIN ROTHENBERG FARLEY & MESITI P.C.

(57) ABSTRACT

Provided is a method, including stretching a polynucleotide over a substrate including a plurality of equally spaced cleavage regions including a plurality of transposases, cleaving the polynucleotide with two or more of the plurality of transposases to form a plurality of polynucleotide fragments, and separating, within the plurality of polynucleotide fragments, a population of longer polynucleotide fragments from a population of shorter polynucleotide fragments. Also provided is a method including stretching a polynucleotide over a substrate including a plurality of equally spaced cleavage regions including a plurality of transposases, cleaving the polynucleotide with two or more of the plurality of transposases to form a plurality of polynucleotide fragments, and separating, within the plurality of polynucleotide fragments, a population of longer polynucleotide fragments from a population of shorter polynucleotide fragments.

23 Claims, 10 Drawing Sheets

(58) Field of Classification Search
USPC .............................................................. 506/4
See application file for complete search history.

(56) References Cited

OTHER PUBLICATIONS

Strecker et al., "RNA-guided DNA insertion with CRISPR-associated Transposases," Science 365:48-53 (2019).

Vo et al., "CRISPR RNA-guided Integrases for High-Efficiency and Multiplexed Bacterial Genome Engineering," Nature Biotechnology 39:480-489 (2021) BioRxiv preprint doi: https://www.biorxiv.org/content/10.1101/2020.07.17.209452v1.

Wan Mengjia et al., "Influence of Concentration on Distribution Properties of Stretched-DNA in the MEC Studied with Fluorescence Imaging and Drop Shape Analyzing," Colloids and Surfaces B: Biointerfaces, vol. 151, No. 3 (2016).

Minsub Han et al., "Effect of Non-Uniform Fields on DNA Entering Non-Channel," Journal of Mechanical Science and Technology, vol. 33, No. 11 (2019).

Annex to Form PCT/ISA/206 Communication Relating to the Results of the Partial International Search of the International Searching Authority for International Application No. PCT/US2021/039019 dated Oct. 20, 2021.

\* cited by examiner

SEPARATING POLYNUCLEOTIDE FRAGMENTS

This application claims priority to U.S. Provisional Patent Application No. 63/048,347, filed Jul. 6, 2020, the entire contents of which are hereby incorporated herein.

BACKGROUND

Many current nucleotide sequencing platforms include preparation of samples involving cleaving sample polynucleotides into fragments. Fragments may then be processed for sequencing, including modifying them through addition of adapters or other indicia to assist in subsequent sequencing. It may be desirable to obtain fragments of a predetermined length. For example, for some sequencing technologies, accuracy decreases when sequencing fragments beyond a certain length. For another example, long enough fragments may be preferred to maximize throughput of sequencing runs. Furthermore, it may be desirable to obtain a population of fragments of within a relatively circumscribed length range. It may also be desirable for sample preparation to include introduction of adapters on opposing ends of fragments that differ from each other.

For library preparation methods including transposases, transposomes are introduced to target polynucleotides in a random manner, such as in solution or random distribution of transposases on a surface, bead, or flowcell. This then leads to a random distribution of fragment sizes. A tight distribution of fragment sizes may involve fragment sizes that are disadvantageously shorter that preferred, whereas the distribution may become disadvantageously broad as one tries to obtain fragments of larger size, such as by titrating the transposome concentration down.

SUMMARY

The following disclosure includes improvements over such shortcomings.

Provided is a method, including stretching a polynucleotide over a substrate including a plurality of equally spaced cleavage regions including a plurality of transposases, cleaving the polynucleotide with two or more of the plurality of transposases to form a plurality of polynucleotide fragments, and separating, within the plurality of polynucleotide fragments, a population of longer polynucleotide fragments from a population of shorter polynucleotide fragments.

In an example, the polynucleotide is double-stranded and the cleaving includes forming complementary ends at a cleavage point and adding adapters to the complementary ends. In another example, the adapters added to the complementary ends are not connected to each other. In still another example, the adapters added to the complementary ends are connected to each other. In yet another example, the cleavage regions include two types of cleavage regions, and the plurality of equally spaced cleavage regions alternate between the two types of cleavage regions.

In a further example, a first type of the two types of cleavage region includes a first type of adapter and a second type of the two types of cleavage region does not include the first type of adapter. In still a further example, the second type of cleavage region includes a second type of adapter and the first type of cleavage region does not include the second type of adapter. In yet a further example, the substrate includes trenches alternating with interstices, and the cleavage regions include surfaces of the trenches and surfaces of the interstices.

In another example, the substrate includes posts alternating with interstices, and the cleavage regions include surfaces of the posts and surfaces of the interstices. In still another example, the substrate includes wells alternating with interstices, and the cleavage regions include surfaces of the wells and surfaces of the interstices In yet another example, the adapters include a hairpin loop. In a further example, the stretching includes bi-directional molecular combing.

In another aspect, provided is a method, including extending an end of a polynucleotide through a pore of a membrane, wherein the polynucleotide is attached to a bead, the pore is narrower than the bead, and a side of the membrane opposite the bead includes a nuclease, and cleaving the polynucleotide with the nuclease.

In an example, the extending includes electrophoresing. In another example, the polynucleotide is double-stranded. In still another example, the nuclease includes a transposase. In yet another example, the polynucleotide is single-stranded. In a further example, the cleaving includes forming a cleaved end and further including adding an adapter to the cleaved end. In still a further example, the polynucleotide is double-stranded and the cleaving includes forming complementary ends and adding adapters to the complementary ends, wherein the adapters are not connected to each other. In yet a further example, the polynucleotide is double-stranded and the cleaving includes forming complementary ends and adding adapters to the complementary ends, wherein the adapters are connected to each other. In another example, the adapters include a hairpin loop.

Still another example further includes releasing the polynucleotide from the bead. Yet another example further includes synthesizing a copy of a strand of the polynucleotide.

BRIEF DESCRIPTION OF THE DRAWINGS

These and other features, aspects, and advantages of the present disclosure will become better understood when the following detailed description is read with reference to the accompanying drawings, wherein.

DETAILED DESCRIPTION

Figure 1:
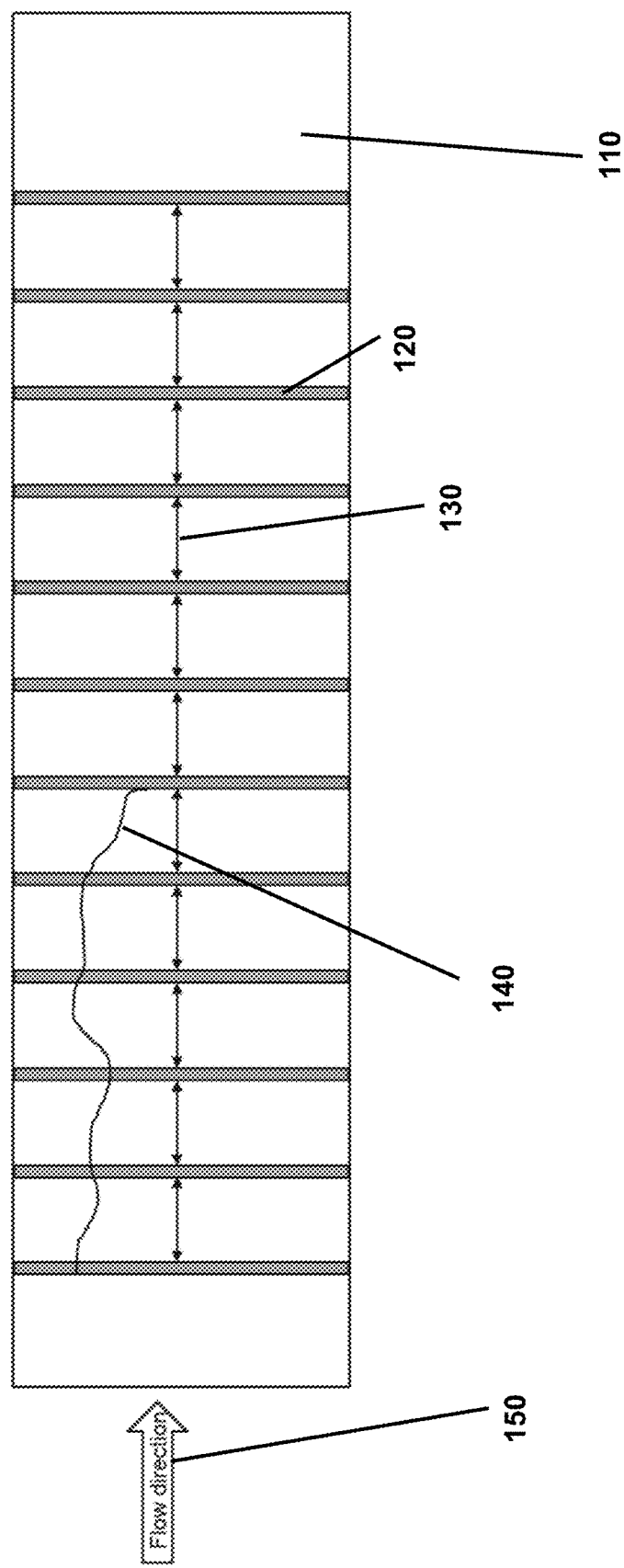
FIG. 1 is an illustration of an example of a polynucleotide stretched over a substrate including a plurality of equally spaced cleavage regions.

As used herein, the terms "includes," "including," "includes," "including," "contains," "containing," "have," "having," and any variations thereof, are intended to cover a non-exclusive inclusion, such that a process, method, product-by-process, or composition of matter that includes, includes, or contains an element or list of elements does not include only those elements but can include other elements not expressly listed or inherent to such process, method, product-by-process, or composition of matter.

As used herein, the singular forms "a", "an" and "the" include plural referents unless the content clearly dictates otherwise. Thus, for example, reference to "a protein" includes a mixture of two or more proteins, and the like.

As used herein, the term "about" or "approximately" means within 5% of a given value or range.

As used herein, the term "nucleic acid" means single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, tetraalkylammonium, $Mg^{2+}$, $Na^+$ and the like. A nucleic acid can be a polynucleotide or an oligonucleotide. A nucleic acid may be composed entirely of deoxyribonucleotides, entirely of ribonucleotides, or chimeric mixtures thereof. The nucleotide monomer units may include any of the nucleotides described herein, including, but not limited to, naturally occurring nucleotides and nucleotides analogs. Nucleic acid may range in size from a few monomeric units, e.g., 5-40, to several thousands of monomeric nucleotide units. Nucleic acids include, but are not limited to, genomic DNA, cDNA, hnRNA, mRNA, rRNA, tRNA, fragmented nucleic acid, nucleic acid obtained from sub-cellular organelles such as mitochondria or chloroplasts, and nucleic acid obtained from microorganisms or DNA or RNA viruses that may be present on or in a biological sample.

As used herein, the term "complementary" when used in reference to a polynucleotide is intended to mean a polynucleotide that includes a nucleotide sequence capable of selectively annealing to an identifying region of a target polynucleotide under certain conditions. As used herein, the term "substantially complementary" and grammatical equivalents is intended to mean a polynucleotide that includes a nucleotide sequence capable of specifically annealing to an identifying region of a target polynucleotide under certain conditions. Annealing refers to the nucleotide base-pairing interaction of one nucleic acid with another nucleic acid that results in the formation of a duplex, triplex, or other higher-ordered structure. The primary interaction may be nucleotide base specific, e.g., A:T, A:U, and G:C, by Watson-Crick and Hoogsteen-type hydrogen bonding. In certain examples, base-stacking and hydrophobic interactions can also contribute to duplex stability.

As used herein, the term "hybridization" refers to the process in which two single-stranded polynucleotides bind non-covalently to form a stable double-stranded polynucleotide. A resulting double-stranded polynucleotide is a "hybrid" or "duplex." Hybridization conditions may include salt concentrations of less than about 1 M, more usually less than about 500 mM and may be less than about 200 mM. A hybridization buffer includes a buffered salt solution such as 5% SSPE, or other such suitable buffers. Hybridization temperatures can be as low as 5° C., but may be greater than 22° C., for example greater than about 30° C., and in one example in excess of 37° C. Hybridizations in some examples are performed under stringent conditions, i.e., conditions under which a probe will hybridize to its target subsequence but will not hybridize to the other, uncomplimentary sequences.

In the context of "polynucleotides," the terms "variant" and "derivative" as used herein refer to a polynucleotide that includes a nucleotide sequence of a polynucleotide or a fragment of a polynucleotide, which has been altered by the introduction of nucleotide substitutions, deletions or additions. A variant or a derivative of a polynucleotide can be a fusion polynucleotide which contains part of the nucleotide sequence of a polynucleotide. The term "variant" or "derivative" as used herein also refers to a polynucleotide or a fragment thereof, which has been chemically modified, e.g., by the covalent attachment of any type of molecule to the polynucleotide. For example, but not by way of limitation, a polynucleotide or a fragment thereof can be chemically modified, e.g., by acetylation, phosphorylation, methylation, etc. The variants or derivatives are modified in a manner that is different from naturally occurring or starting nucleotide or polynucleotide, either in the type or location of the molecules attached. Variants or derivatives further include deletion of one or more chemical groups which are naturally present on the nucleotide or polynucleotide. A variant or a derivative of a polynucleotide or a fragment of a polynucleotide can be chemically modified by chemical modifications using techniques known to those of skill in the art, including, but not limited to specific chemical cleavage, acetylation, formulation, etc. Further, a variant or a derivative of a polynucleotide or a fragment of a polynucleotide can contain one or more dNTPs or nucleotide analogs. A polynucleotide variant or derivative may possess a similar or identical function as a polynucleotide or a fragment of a polynucleotide described herein. A polynucleotide variant or derivative may possess an additional or different function compared with a polynucleotide or a fragment of a polynucleotide described herein.

As used herein, the term "dNTP" refers to deoxynucleoside triphosphates. NTP refers to ribonucleotide triphosphates. The purine bases (Pu) include adenine (A), guanine (G) and derivatives and analogs thereof. The pyrimidine bases (Py) include cytosine (C), thymine (T), uracil (U) and derivatives and analogs thereof. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

As used herein, "nucleic acid fragment" refers to a synthetic or natural molecule including a covalently linked sequence of nucleotides. The nucleotides can be joined by a phosphodiester bond between the 3' position of the deoxyribose or ribose of one nucleotide and the 5' position of the deoxyribose or ribose of the adjacent nucleotide. A nucleic acid fragments can include natural (e.g., a, G, C, T or U) or modified bases (e.g., 7-deazaguanosine, inosine). In addition, the bases in a nucleic acid fragments can be joined by a linkage other than a phosphodiester bond, so long as it does not interfere with hybridization of the nucleic acid fragment. Thus, nucleic acid fragments can be peptide nucleic acids in which one or more of the constituent bases are joined by peptide bonds rather than phosphodiester linkages.

As used herein, "nuclease" refers to any enzyme that cleaves nucleic acids. Nucleases belong to a class of enzymes called hydrolases and are usually specific in action, ribonucleases acting preferentially upon ribonucleic acids (RNA) and deoxyribonucleases acting preferentially upon deoxyribonucleic acids (DNA). Some enzymes having a general action (e.g., phosphoesterases, which hydrolyze phosphoric acid esters) can be called nucleases because nucleic acids are susceptible to their action As used herein, the term "nucleotide analogs" refers to synthetic analogs having modified nucleotide base portions, modified pentose portions, and/or modified phosphate portions, and, in the case of polynucleotides, modified internucleotide linkages. Modified internucleotide linkages include phosphate analogs, analogs having achiral and uncharged intersubunit linkages, and uncharged morpholino-based polymers having achiral intersubunit linkages. Some internucleotide linkage analogs include morpholidate, acetal, and polyamide-linked heterocycles. Examples of phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., H+, NH4+, Na+, if such counterions are present. Examples of modified nucleotide base portions include but are not limited to 5-methylcytosine (5mC); C-5-propynyl analogs, including but not limited to C-5 propynyl-C and C-5 propynyl-U; 2,6-diaminopurine, also known as 2-amino adenine or 2-amino-dA); hypoxanthine, pseudouridine, 2-thiopyrimidine, isocytosine (isoC), 5-methyl isoC, and isoguanine (isoG). Examples of modified pentose portions include but are not limited to, locked nucleic acid (LNA) analogs including without limitation Bz-A-LNA, 5-Me-Bz-C-LNA, dmf-G-LNA, and T-LNA, and 2'- or 3'-modifications where the 2'- or 3'-position is hydrogen, hydroxy, alkoxy (e.g., methoxy, methoxy-ethyl, —O-methyl, ethoxy, allyloxy, isopropoxy, butoxy, isobutoxy and phenoxy), azido, amino, alkylamino, fluoro, chloro, or bromo. Other examples include 2-aminopurine; 5-bromo du; deoxyUridine; deoxyInosine; hydroxymethyl dC; 5-methyl dC; 5-Nitroindole; 5-hydroxybutynl-2'-deoxyuridine; and 8-aza-7-deazaguanosine.

As used herein, the terms "ligation," "ligating," and grammatical equivalents thereof are intended to mean to form a covalent bond or linkage between the termini of two or more nucleic acids, e.g., oligonucleotides and/or polynucleotides, in some instances in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. The term "ligation" also encompasses non-enzymatic formation of phosphodiester bonds, as well as the formation of non-phosphodiester covalent bonds between the ends of oligonucleotides, such as phosphorothioate bonds, disulfide bonds, and the like.

As used herein, "primer" refers to a single-stranded oligonucleotide that is extended by covalent bonding of nucleotide monomers during amplification or polymerization of a nucleic acid molecule. A primer can be naturally occurring as in a purified restriction digest or produced synthetically, which is capable of acting as a point of initiation of sample-dependent nucleic acid synthesis. The primer may be either single-stranded or double-stranded and, in particular examples, must be sufficiently long to prime the synthesis of the desired extension product in the presence of the chosen polymerase. The exact length of the primer will depend upon many factors, including hybridization and polymerization temperatures, source of primer and the method used. For example, a primer can include about at least 15-75 nucleotides, although it may contain fewer or more nucleotides.

As used herein, the term "adaptor" is a single-stranded or a double-stranded nucleic acid molecule that can be linked to the end of other nucleic acids. Two "adaptors" may be ends of a hairpin loop. Adaptors may be strands of a double-stranded nucleic acid (e.g., oligonucleotides) that include single-stranded nucleotide overhangs at the 5' and/or 3' ends. In a further example, the single stranded overhangs may be 1, 2 or more nucleotides.

As used herein, "sample" refers to material that includes double-stranded or single-stranded nucleic acid molecules which are to be cleaved, amplified, hybridized, purified, isolated, synthesized, sequenced and/or otherwise targeted for a specific use. Samples can include all or a portion of a gene, a regulatory sequence, genome, genomic DNA, cDNA, transcriptome, RNA including mRNA or rRNA. It may be any length, with the understanding that longer sequences are more specific.

For instance, a sample can be a "library" or "nucleic acid library," a set of nucleic acid molecules (e.g., circular or linear) representative of all or a significant portion of the DNA content of an organism (e.g., "genomic library") or a set of nucleic acid molecules representative of all or a significant portion of the expressed genes (e.g., "cDNA library") in a cell, tissue, organ, or organism. A nucleic acid library may be a eukaryotic cDNA library, eukaryotic genomic library, prokaryotic genomic library, random semi-random nucleic acid library, or semi-random nucleic acid library. Such libraries may or may not be contained in one or more vectors.

As used herein "solid support," "support," and "substrate" refers to any material that provides a solid or semi-solid structure with which another material can be attached including but not limited to smooth supports (e.g., metal, glass, plastic, silicon, and ceramic surfaces) as well as textured and porous materials. Substrate materials include, but are not limited to acrylics, carbon (e.g., graphite, carbon-fiber), cellulose (e.g., cellulose acetate), ceramics, controlled-pore glass, cross-linked polysaccharides (e.g., agarose or SEPHAROSE®), gels, glass (e.g., modified or functionalized glass), gold (e.g., atomically smooth Au(111)), graphite, inorganic glasses, inorganic polymers, latex, metal oxides (e.g., SiO2, TiO2, stainless steel), metalloids, metals (e.g., atomically smooth Au(111)), mica, molybdenum sulfides, nanomaterials (e.g., highly oriented pyrolitic graphite (HOPG) nanosheets), nitrocellulose, NYLON®, optical fiber bundles, organic polymers, paper, plastics, polacryloylmorpholide, poly(4-methylbutene), poly(ethylene terephthalate), poly(vinyl butyrate), polybutylene, polydimethylsiloxane (PDMS), polyethylene, polyformaldehyde, polymethacrylate, polypropylene, polysaccharides, polystyrene, polyurethanes, polyvinylidene difluoride (PVDF), quartz, rayon, resins, rubbers, semiconductor material, silica, silicon (e.g., surface-oxidized silicon), sulfide, and TEFLON®.

Substrates need not be flat and can include any type of shape including spherical shapes (e.g., beads) or cylindrical shapes (e.g., fibers). Materials attached to solid supports may be attached to any portion of the solid support (e.g., may be attached to an interior portion of a porous solid support material).

Substrates may be patterned, where a pattern (e.g., stripes, swirls, lines, triangles, rectangles, circles, arcs, checks, plaids, diagonals, arrows, squares, cross-hatches, trenches, posts, wells) is etched, printed, treated, sketched, cut, carved, engraved, imprinted, fixed, stamped, coated, embossed, embedded, or layered onto a substrate. The pattern can include one or more cleavage regions or modified regions on the substrate.

As used herein, "pitch" refers to the distance between corresponding points on two juxtaposed cleavage regions on a substrate having a repeated pattern of cleavage regions. For example, the corresponding points can be the centers of two adjacent cleavage regions (e.g., center to center distance). In another example, the pitch can be measured from the left most edge of a first cleavage region to the left most edge of an adjacent cleavage region such that the distance includes the gap between the cleavage regions as well as the length of one of the cleavage regions. The pitch can be, for example, at least about 1 nm to about 1,000 µm.

A biological material is "attached" to a substrate when it is associated with the solid substrate through a stable chemical or physical interaction. In some examples, the attachment is through a covalent bond. However, attachments need not be covalent or permanent. In one example, materials are attached to a substrate through a "spacer molecule" or "linker group." Such spacer molecules are molecules that have a first portion that attaches to the biological material and a second portion that attaches to the substrate. Thus, when attached to the substrate, the spacer molecule separates the substrate and the biological materials, but is attached to both. Methods of attaching biological material (e.g., nucleic acid, affinity ligand receptor, enzyme, chemical hydroxyl radical generator) to a substrate may include but are not limited to chemical coupling.

As used herein, the term "surface" refers to a part of a support structure (e.g., substrate) that is accessible to contact with reagents, beads or analytes. The surface can be at least partially flat or planar. Alternatively, the surface can be rounded or contoured. Examples of contours that can be included on a surface are wells, depressions, pillars, ridges, channels or the like. Examples of materials that can be used as a support structure include, but are not limited to acrylics, carbon (e.g., graphite, carbon-fiber), cellulose (e.g., cellulose acetate), ceramics, controlled-pore glass, cross-linked polysaccharides (e.g., agarose or SEPHAROSE®), gels, glass (e.g., modified or functionalized glass), gold (e.g., atomically smooth Au(111)), graphite, inorganic glasses, inorganic polymers, latex, metal oxides (e.g., SiO2, TiO2, stainless steel), metalloids, metals (e.g., atomically smooth Au(111)), mica, molybdenum sulfides, nanomaterials (e.g., highly oriented pyrolitic graphite (HOPG) nanosheets), nitrocellulose, NYLON®, optical fiber bundles, organic polymers, paper, plastics, polacryloylmorpholide, poly(4-methylbutene), polyethylene terephthalate), poly(vinyl butyrate), polybutylene, polydimethylsiloxane (PDMS), polyethylene, polyformaldehyde, polymethacrylate, polypropylene, polysaccharides, polystyrene, polyurethanes, polyvinylidene difluoride (PVDF), quartz, rayon, resins, rubbers, semiconductor material, silica, silicon (e.g., surface-oxidized silicon), sulfide, and TEFLON®. A single material or mixture of several different materials can form a surface in accordance with the present disclosure. The terms "surface" and "substrate" are used interchangeably herein.

As used herein, the term "tagmentation," "tagment," or "tagmenting" refers to transforming a nucleic acid, e.g., a DNA, into adaptor-modified templates in solution ready for cluster formation and sequencing by the use of transposase mediated fragmentation and tagging. This process often involves the modification of the nucleic acid by a transposome complex including transposase enzyme complexed with adaptors including transposon end sequence. Tagmentation results in the simultaneous fragmentation of the nucleic acid and ligation of the adaptors to the 5' ends of both strands of duplex fragments. Following a purification step to remove the transposase enzyme, additional sequences are added to the ends of the adapted fragments by PCR.

As used herein, the term "transposome complex" refers to a transposase enzyme non-covalently bound to a double stranded nucleic acid. For example, the complex can be a transposase enzyme preincubated with double-stranded transposon DNA under conditions that support non-covalent complex formation. Double-stranded transposon DNA can include, without limitation, Tn5 DNA, a portion of Tn5 DNA, a transposon end composition, a mixture of transposon end compositions or other double-stranded DNAs capable of interacting with a transposase such as the hyperactive Tn5 transposase.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target nucleic acid with which it is incubated, for example, in an in vitro transposition reaction. A transposase as presented herein can also include integrases from retrotransposons and retroviruses. Although many examples described herein refer to Tn5 transposase and/or hyperactive Tn5 transposase, it will be appreciated that any transposition system that is capable of inserting a transposon end with sufficient efficiency to 5'-tag and fragment a target nucleic acid for its intended purpose can be used in accordance with the present disclosure. In particular examples, a transposition system is capable of inserting the transposon end in a random or in an almost random manner to 5'-tag and fragment the target nucleic acid.

As used herein, the term "transposition reaction" refers to a reaction wherein one or more transposons are inserted into target nucleic acids, e.g., at random sites or almost random sites. Essential components in a transposition reaction are a transposase and DNA oligonucleotides that exhibit the nucleotide sequences of a transposon, including the transferred transposon sequence and its complement (the non-transferred transposon end sequence) as well as other components needed to form a functional transposition or transposome complex. The DNA oligonucleotides can further include additional sequences (e.g., adaptor or primer sequences) as needed or desired. In some examples, the method provided herein is exemplified by employing a transposition complex formed by a hyperactive Tn5 transposase and a Tn5-type transposon end or by a MuA transposase and a Mu transposon end including R1 and R2 end sequences. However, any transposition system that is capable of inserting a transposon end in a random or in an almost random manner with sufficient efficiency to 5'-tag and fragment a target DNA for its intended purpose can be used in accordance with the present disclosure. Examples of transposition systems may include but are not limited to *Staphylococcus aureus* Tn552, TyI, Transposon Tn7, TnIO and ISIO, Mariner transposase, Tci, P Element, TnJ, bacterial insertion sequences, retroviruses, and retrotransposon of yeast. The method for inserting a transposon end into a target sequence can be carried out in vitro using any suitable transposon system for which a suitable in vitro transposition system is available or that can be developed based on knowledge in the art. In general, a suitable in vitro transposition system for use in the methods provided herein involves, at a minimum, a transposase enzyme of sufficient purity, sufficient concentration, and sufficient in vitro transposition activity and a transposon end with which the transposase forms a functional complex with the respective transposase that is capable of catalyzing the transposition reaction. Suitable transposase transposon end sequences that can be used in accordance with the present disclosure include but are not limited to wild-type, derivative or mutant transposon end sequences that form a complex with a transposase chosen from among a wild-type, derivative or mutant form of the transposase.

The term "transposon end" (TE) refers to a double-stranded nucleic acid, e.g., a double-stranded DNA, that exhibits only the nucleotide sequences (the "transposon end sequences") that are involved to form the complex with the transposase or integrase enzyme that is functional in an in vitro transposition reaction. In some examples, a transposon end is capable of forming a functional complex with the transposase in a transposition reaction. As non-limiting examples, transposon ends can include the 19-bp outer end ("OE") transposon end, inner end ("IE") transposon end, or "mosaic end" ("ME") transposon end recognized by a wild-type or mutant Tn5 transposase, or the R1 and R2 transposon end. Transposon ends can include any nucleic acid or nucleic acid analogue suitable for forming a functional complex with the transposase or integrase enzyme in an in vitro transposition reaction. For example, the transposon end can include DNA, RNA, modified bases, non-natural bases, modified backbone, and can include nicks in one or both strands. Although the term "DNA" is sometimes used in the present disclosure in connection with the composition of transposon ends, it should be understood that any suitable nucleic acid or nucleic acid analogue can be utilized in a transposon end.

As used herein, the term "label" refers to a process in which a component, e.g., an adaptor, is modified, e.g., binding to another molecule, so that to facilitate separation of the component and its associated elements.

Sequencing platforms that employ closed-ended double stranded sequencing templates may include two different adaptor sequences at the ends of the sequencing templates. Such end asymmetry enables a single sequencing polymer and polymerase to bind to only one end of the close-ended sequencing template, and generate only one sequence read per template molecule. However, such end asymmetry is not currently employed by such sequencing platforms for library preparations. Instead, these sequencing platforms have symmetrical ends where the sequencing primer can bind at either end of the sequencing template, thus introducing Poisson artefacts to sequencing. In other words, some of the sequencing template will have no primer/polymerase bound, some sequencing templates will have one primer bound, and some sequencing templates will have two primers bound at either end of the sequencing template. With use of closed-ended sequencing templates that have asymmetric ends, these Poisson artefacts can be avoided. Accordingly, the methods of the disclosure provide a notable improvement over the state of the art by providing for the generation of closed-ended double stranded templates that have asymmetric ends by significantly increasing the conversion yield for sequencing libraries. Further, the methods of the disclosure provide for steps that can be performed in situ in the wells of a sequencing platform, allowing for library preparation to be conducted on the sequencing platform.

"Molecular Combing" or "Chromosome Combing" or "Nucleic Acid Combing" refer to a method including linearly stretching one or more sample nucleic acids transversely over a surface patterned with cleavage regions. A nucleic acid molecule may bind by one or both extremities (or regions proximal to one or both extremity) to a modified surface (e.g., silanized glass) and then be substantially uniformly stretched and aligned by a receding air/water interface. The stretching method has a high resolution ranging from a few kilobases to megabases.

Molecular combing may include a fluid flow method or application of weak forces such as electrophoresis or receding meniscus.

A fluid flow method of molecular combing can be done by combing by capillary flow or combing by force flow. In a fluid flow example, nucleic acid is stretched in solution as it flows through a microfluidic channel or it is stretched on a solid surface. Generally microfluidic or nanofluidic flow chambers can be used.

The percentage of fully-stretched nucleic acid molecules depends on the length of the nucleic acid molecules. Generally, the longer the nucleic acid molecules, the easier it is to achieve a complete stretching. For example, according to Conti, et al., over 40% of a 10 kb DNA molecules could be routinely stretched with some conditions of capillary flow, while only 20% of a 4 kb molecules could be fully stretched using the same conditions. For shorter nucleic acid fragments, the stretching quality may be improved with the stronger flow induced by dropping coverslips onto the slides.

In an example of molecular combing, a nucleic acid molecule may be attached to a substrate at one end and stretched by one or more of various weak forces, such as, for example, electric force, surface tension, or optical force. In this example, one end of the nucleic acid molecule is first anchored to a surface. For example, the molecule can be attached to a hydrophobic surface (e.g., modified glass) by adsorption. The anchored nucleic acid molecules can be stretched by a receding meniscus, evaporation, or by nitrogen gas flow.

Nucleic acids can be stretched by a factor of 1.5 times the crystallographic length of the nucleic acid. In another example, the nucleic acid in solution (e.g., has a random-coil structure) is stretched by retracting the meniscus of a solution at a constant rate (e.g., 300 μm/s). Without being bound by a particular theory, the ends of the nucleic acid strands in one example are believed to be frayed (e.g., open and exposing polar groups) that bind to ionisable groups coating a modified substrate (e.g., silanized glass plate) at a pH below the pKa of the ionisable groups (e.g., ensuring they are charged enough to interact with the ends of the nucleic acid molecule). The rest of the nucleic acid molecule (e.g., dsDNA) may be unable to form these interactions. As the meniscus retracts, surface retention creates a force that acts on the nucleic acid molecule to retain it in the liquid phase; however this force is inferior to the strength of the nucleic acid molecule's attachment; the result is that the nucleic acid molecule is stretched as it enters the air phase; as the force acts in the locality of the air/liquid phase, it is invariant to different lengths or conformations of the nucleic acid molecule in solution, so the nucleic acid molecule of any length will be stretched the same as the meniscus retracts. As this stretching is constant along the length of a the nucleic acid molecule, distance along the strand can be related to base content; 6 µm is approximately equivalent to 20 kb.

The pH of the solution used in a receding meniscus method can affect the efficiency of nucleic acid binding to the substrate. On hydrophobic surfaces binding efficiency may be reached at a pH of approximately 5.5. For example, at pH 5.5, approximately 40-kbp DNA is 10 times more likely to bind by an extremity than by a midsegment.

Figure 7:
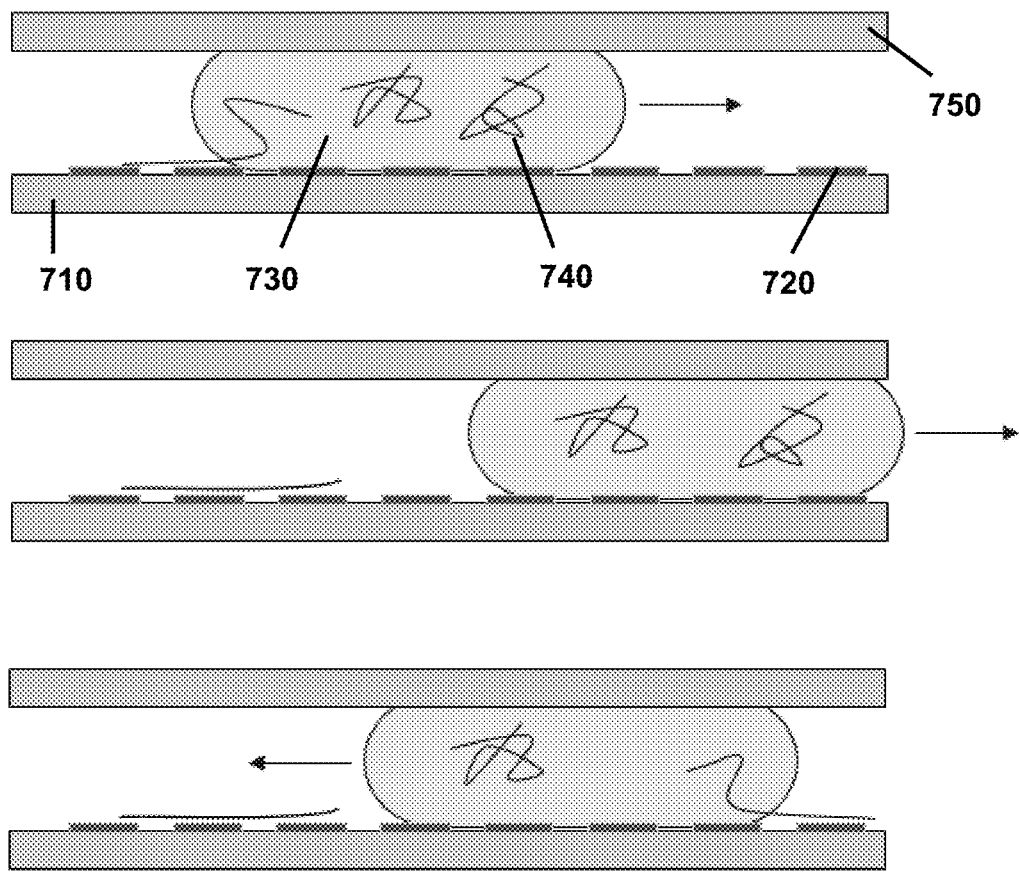
FIG. 7 is an illustration of an example of stretching a polynucleotide over a substrate including a plurality of equally spaced cleavage regions wherein stretching includes bi-directional molecular combing.

In another example, a nucleic acid molecule may be stretched by dissolving nucleic acid molecules in a drop of buffer and running down a sloping substrate very slowly. In a further example, nucleic acids may be embedded in agarose blocks, placed on a substrate. The agarose block including the nucleic acid is then melted and dragged along the substrate with a second substrate (e.g., coverslip). In another example, a second substrate may be moved in more than one direction to elicit enhanced molecular combing of polynucleotides included in a buffer. Movement of a second substrate overlying a first, with a buffer therebetween containing polynucleotides, may induce combing of some but not all polynucleotides within the buffer onto the first substrate. Attachment of further polynucleotides to the first substrate may be induced by changing the direction of movement of the second substrate such as, in an example, in the opposite direction from its first movement, though another direction or directions may be used as a second or subsequent movement of the second substrate. A non-limiting example of such bi-directional combing is illustrated in FIG. 7. In the upper panel, a buffer 730 including polynucleotides 740 is between a first substrate 710 including cleavage regions 720 and a second substrate 750. As the first 710 and second 750 substrates move in relation to each other, some polynucleotides 740 attach and are combed onto the first substrate 710 (middle panel). As the first 710 and second 750 substrates move in relation to each other but in a different direction, additional polynucleotides 740 attach and are combed onto the first substrate 710 (bottom panel).

Another example includes reversibly orienting long-chain nucleic acids on hydrophilic substrates without a fluid meniscus. End-tethered nucleic acid mushrooms are elongated by a hydrodynamic flow in the presence of trivalent cations, resulting in electrostatic adsorption of the stretched nucleic acid to the substrate. By complexation of the cations the part of the nucleic acid molecule which is non-specifically bound to the surface desorbs quantitatively, and the mushroom conformation is restored. With the use of multiple deposition-combing steps, combined with a final desorption step, tethering densities higher than attainable with single deposition steps can be obtained.

As disclosed herein, nucleic acid combed on a substrate may be cleaved into substantially uniform fragments by enzymatic cleavage (e.g., nucleases, transposases). As disclosed herein, nucleases may be associated (covalently or non-covalently) with the patterned cleavage regions. Nucleases suitable for use in the methods described herein include double-stranded nucleases and single-stranded nucleases (e.g., nucleases that preferentially digest single-stranded nucleic acid regions, referred to herein as "single-stranded nucleases.")

The double-stranded nucleases can be non-specific, digesting both RNA and DNA, and/or variants thereof. In other examples, the double-stranded nucleases preferentially digest double-stranded RNA, e.g., "double-stranded RNases," or preferentially digest double-stranded DNA, e.g., "double-stranded DNases." Finally, nucleases may be exonucleases that digest only from the 5'-end of a polynucleotide, e.g., 5' double-stranded nucleases, the 3'-end of a polynucleotide, e.g., 3' double-stranded nucleases, or both ends of a double-stranded polynucleotide. Alternatively, endonucleases that cleave at locations within a nucleic acid strand can be used.

The single-stranded nucleases can be non-specific, digesting both RNA and DNA, and/or variants thereof. In other examples, the single-stranded nucleases preferentially digest single-stranded RNA, e.g., "single-stranded RNases," or preferentially digest single-stranded DNA, e.g., "single-stranded DNases." Finally, nucleases may digest only from the 5'-end of a polynucleotide, e.g., 5' single-stranded nucleases, the 3'-end of a polynucleotide, e.g., 3' single-stranded nucleases, or both ends of a single-stranded polynucleotide.

In an example, the nuclease digests single-stranded (e.g., unduplexed) nucleic acids and/or single-stranded regions of nucleic acids of nucleic acid molecules and samples. In an alternative example, the nuclease selectively digests the single-stranded nucleic acids of the sample. In yet another example, the nuclease selectively digests the single-stranded nucleic acids of the unbound nucleic acid molecules. The specific nuclease selected for nuclease treatment depends on the desired selectivity (e.g., nucleic acid molecule and/or sample digestion) and nature of the nucleic acids making up the nucleic acid molecule and sample.

RNase A is an example of an RNA nuclease that can be used to remove single-stranded RNA. RNase A effectively recognizes and cuts single-stranded RNA, including RNA in RNA:DNA hybrids that is not in a perfect double-stranded complex. Moreover, RNA bulges, loops, and even single base mismatches can be recognized and cleaved by RNase A. S1 nuclease and Mung Bean nuclease are examples of DNA nucleases with similar properties for single-stranded DNA.

Non-limiting examples of nucleases that may be used in accordance with the present disclosure include S1 nuclease, Mung-bean nuclease, Ribonuclease A, RNAse T1, Exonuclease I, RNase ONE®, Deoxyribonuclease I, DNA Nuclease BAL 31, Exonuclease III, and transposases such as Tn5, MuA, Tn552, TyI, Transposon Tn7, TnlO and ISlO, Mariner transposase, Tci, P Element, TnJ, bacterial insertion sequences, retroviruses, and retrotransposon of yeast or other transposases.

A hairpin loop, including an adapter at each ends, may be attached to a double stranded nucleic acid template that has free 5' and 3' ends. The double stranded nucleic acid template may be ds DNA, ds RNA, or a chimeric mixture of DNA and RNA. The nucleotides of the nucleic acid may be included of naturally occurring nucleotides, e.g., A, G, C, T, and U, that are joined together via phosphodiester bond linkages. Alternatively, one or more nucleotides of the nucleic acid may be modified in some manner (e.g., a nucleotide analog). Further, the nucleotides may be linked together by phosphorothioate linkages in addition to phosphodiester linkages. The free 5' and 3' ends of the double stranded nucleic acid template may be blunt, or have overhang of one or more unmatched bases (e.g., a 3' overhang or a 5' overhang). In a certain example, the free 5' and 3' ends of the double stranded nucleic acid template includes a 3' overhang of one or more adenine bases. In a further example, the 5' and 3' ends of the double stranded nucleic acid template have been dephosphorylated and end repaired.

A nucleic acid-based hairpin loop includes a sequence that loops back on itself so that the adapters at its 5' and 3' ends can be attached (e.g., ligated, such as by a transposase) to 3' and 5' ends, respectively, of a double stranded polynucleotide. A non-limiting example of a hairpin loop is a stem-and-loop structure. In an example, a double-stranded polynucleotide may have a pair of adapters attached to each of its opposing ends, wherein the pair of adapters attached to each opposing end are connected to each other as ends of a hairpin loop. The double-stranded polynucleotide between and connected to the pair of opposing hairpin loops may form a dumbbell structure, an example of which is illustrated in FIG. 8B. A nucleic acid-based hairpin loop can have any sequence, or can be designed to include a target sequence. Examples of target sequences include, but not limited to, common primer sequence(s), universal sequencing primer sequence(s), bar code sequence(s), restriction enzyme sequence(s), TelN recognition sequence(s), or any combination of the foregoing. A nucleic acid-based hairpin loop may be attached to a double stranded nucleic acid template by a transposome. A nucleic acid-based hairpin loop may further include a label, so as to allow for detection and/or purification of adaptor containing sequences, such as adaptors attached to nucleic acid templates. A nucleic acid-base hairpin loop includes a sequence that loops back on itself so that the adaptor ends can be attached to the strands of double stranded polynucleotide. For the purposes of this disclosure a nucleic acid-based hairpin loop can be Y-shaped and a portion of its sequence may form a hairpin loop. In an example, adapters comprising a Y-shaped hairpin loop can be used to generate an asymmetric closed-ended double stranded nucleic acid template from a double stranded nucleic acid template having free 5' and 3' ends.

In some examples, a nucleic acid-based hairpin loop may be attached to a polynucleotide by use of a ligase. Examples of ligases, include but are not limited to, DNA ligases, like T4 DNA ligase, E. Coli DNA ligase, Ampligase DNA Ligase, T3 DNA ligase, T7 DNA ligase, and Taq DNA Ligase; and RNA ligases, like T4 RNA Ligase 1, T4 RNA Ligase 2, RtcB Ligase, and M. thermoautotrophicum Ligase.

Many of the steps of the methods disclosed herein can be performed within the well of a sequence platform, like a zero mode waveguide (ZMW) well. For example, a ZMW well can be loaded with the double stranded nucleic acid template including the attached hairpin loop, a polymerase, TelN Protelomerase, one or more sequencing primer(s), and reaction buffers containing dNTPS or NTPS. In the first read, the 3' end of the nucleic acid hairpin sequence is extended generating a duplex template including a closed hairpin (the "hairpin end") and the other end of the duplex includes a free 3'-strand end and a free 5'-strand end (the "free end"). In doing so, a TelN recognition sequence is generated which is acted on by the TelN enzyme, thereby forming a closed-ended double stranded nucleic acid template that is bound by the sequencing primer and sequencing is then carried out in the automated platform in subsequent reads.

A nucleic acid-based hairpin loop may be attached to a double stranded nucleic acid template via transposase mediated tagmentation or transposition reaction. Transposomes have free DNA ends and insert randomly into DNA in a 'cut and paste' reaction. Because the DNA ends are free, this effectively fragments the DNA while adding on the nucleic acid-based hairpin loop. Transposition complexes, suitable for use in the methods provided herein, include, but are not limited to, those formed by a hyperactive Tn5 transposase and a Tn5-type transposon end or by a MuA transposase and a Mu transposon end including R1 and R2 end sequences, a transposase Tn3, and a Sleeping Beauty transposase. However, any transposition system that is capable of inserting a transposon end with sufficient efficiency to attach nucleic acid-based hairpin loop to ends of a double stranded nucleic acid template. Other examples of known transposition systems that may be used in the provided methods include, but are not limited to, *Staphylococcus aureus* Tn552, Ty1, Transposon Tn7, Tn/O and IS10, Mariner transposase, Tc1, P Element, Tn3, bacterial insertion sequences, retroviruses, and retrotransposon of yeast. In a particular example, the tagmented template includes a mosaic end (ME) sequence, and the transposase is a Tn5 transposase.

A number of substrates (e.g., solid supports) are suitable for use with the methods as disclosed herein. In an example, the substrate is modified to contain patterns—e.g., trenches, patterns, layers, wells, or other configurations. In particular examples, there is a general direct correlation between the size of the pitch or gap separating cleavage regions and the size of the resultant at least substantially uniform nucleic acid fragment (e.g., a pitch of 100 nm may produce fragments of approximately 300 bases, a pitch of 1 μm may produce fragments of approximately 3 kilobases, a pitch of 10 μm may produce fragments of approximately 30 kilobases, etc.). The pitch can be effectively equivalent to the gap in examples wherein the width of the cleavage region is relatively narrow.

The pattern can have a pitch or gap from at least about 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1,000 nm. Alternatively or additionally, the pattern can have a pitch or gap less than at least about 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1,000 nm. The pattern can be stripes, swirls, lines, triangles, rectangles, circles, arcs, checks, plaids, diagonals, arrows, squares, or cross-hatches. The pattern can be linear or curved. The pattern can be repeating, non-repeating, or a mixture of two patterns (e.g., lines of different width).

In another example, the pattern can have a pitch or gap from at least about 10 to about 20, about 10 to about 30, about 10 to about 40, about 10 to about 50, about 10 to about 60, about 10 to about 70, about 10 to about 80, about 10 to about 90, or about 10 to about 100 μm. In a further example, the pattern can have a pitch or gap from at least about 100 to about 200, about 100 to about 300, about 100 to about 400, about 100 to about 500, about 100 to about 600, about 100 to about 700, about 100 to about 800, about 100 to about 900, or about 100 to about 1,000 µm. Alternatively, the pattern can have a pitch or gap from at least about 10 to about 20, about 10 to about 30, about 10 to about 40, about 10 to about 50, about 10 to about 60, about 10 to about 70, about 10 to about 80, about 10 to about 90, or about 10 to about 100 nm. In a further example, the pattern can have a pitch or gap from at least about 100 to about 200, about 100 to about 300, about 100 to about 400, about 100 to about 500, about 100 to about 600, about 100 to about 700, about 100 to about 800, about 100 to about 900, or about 100 to about 1,000 nm.

In another example, the pattern can have a pitch or gap from at least about 10 nm to 20 µm, about 10 nm to about 30 µm, about 10 nm to about 40 µm, about 10 nm to about 50 µm, about 10 nm to about 60 µm, about 10 nm to about 70 µm, about 10 nm to about 80 µm, about 10 nm to about 90 µm, or about 10 nm to about 100 µm. In another example, the pattern can have a pitch or gap from at least about 100 µm to about 10 µm, about 100 nm to about 20 µm, about 100 nm to about 30 µm, about 100 nm to about 40 µm, about 100 nm to about 50 µm, about 100 nm to about 60 µm, about 100 nm to about 70 µm, about 100 nm to about 80 µm, about 100 nm to about 90 µm, or about 100 nm to about 100 µm. In a still further example, the pattern can have a pitch or gap from at least about 100 to about 200 µm, about 100 nm to about 300 µm, about 100 nm to about 400 µm, about 100 nm to about 500 µm, about 100 nm to about 600 µm, about 100 nm to about 700 µm, about 100 nm to about 800 µm, about 100 nm to about 900 µm, or about 100 nm to about 1,000 µm.

The substrate may include a modified surface (e.g., silanized). Silanization includes covering a surface through self-assembly with silane-like molecules. Mica, glass, quartz, and metal oxide surfaces (e.g., $SiO_2$, $TiO_2$, stainless steel) may be silanized, because they contain hydroxyl groups which attack and displace the alkoxy groups on the silane thus forming a covalent —Si—O—Si— bond. It should be appreciated that any substrate material with hydroxyl groups can be silanized. In an example, only part of the substrate is modified. In another example, a portion of the substrate is modified and has a pattern of cleavage regions. In another example, nucleic acids can be combed on cetyltrimethyl ammonium bromide (CTAB)-coated glass surfaces (e.g., uniform and straight on CTAB-coated surfaces.) It should be appreciated that on hydrophobic silanized surfaces, a nucleic acid may be stuck along its full length with a very high density of attachment points. In contrast, when the substrate (e.g., glass) is coated with hydrophobic polymers (e.g., polymethylmetacrylate (PMMA), polydimethyl-siloxane (PDMS) or polystyrene) the combed nucleic acid may attach in only a few places to the surface. In an example, the pH is lowered to a value of pH<6 (e.g., pH=2, 3, 4, 4.5, 5, 5.5, 5.7) during combing, the tethering can be restricted to only the extremities of the nucleic acid.

Suitable substrates include materials including but not limited to borosilicate glass, agarose, sepharose, magnetic beads, polystyrene, polyacrylamide, membranes, silica, semiconductor materials, silicon, organic polymers, ceramic, glass, metal, plastic polycarbonate, polycarbonate, polyethylene, polyethyleneglycol terephthalate, polymethylmethacrylate, polypropylene, polyvinylacetate, polyvinylchloride, polyvinylpyrrolidinone, and soda-lime glass. The substrate body may be in the form of a bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial. The substrate can be a singular discrete body (e.g., a single tube, a single bead), any number of a plurality of substrate bodies (e.g., a rack of 10 tubes, several beads), or combinations thereof (e.g., a tray includes a plurality of microtiter plates, a column filled with beads, a microtiter plate filed with beads). In an example, the substrate is glass. In another example, the substrate is modified glass, for example silanized glass.

The nucleic acid sample can be immobilized, coated on, bound to, stuck, adhered, or attached to any of the forms of substrates described herein (e.g., bead, box, column, post, trench, well, cylinder, disc, dish (e.g., glass dish, PETR1 dish), fiber, film, filter, microtiter plate (e.g., 96-well microtiter plate), multi-bladed stick, net, pellet, plate, ring, rod, roll, sheet, slide, stick, tray, tube, or vial). In particular, particles or beads can be a component of a gelling material or can be separate components such as latex beads made of a variety of synthetic plastics (e.g., polystyrene).

Surface of a substrate including cleavage regions may be modified to contain sites for later association of nucleases. These sites may include physically altered sites, e.g., physical configurations such as wells, posts, trenches, or small depressions in the substrate, such as chemically functionalized sites, electrostatically altered sites, hydrophobically/hydrophilically functionalized sites, or spots of adhesive, or any other modification for coupling a plurality of nucleases, such as transposases, onto regions of the substrate intended as cleavage regions. Such regions be chemically functionalized, cross-linking agents may be used, with a complementing chemically functionalized or cross-linking capability attached to or included in a nuclease, to permit covalent attachment of nucleases to cleavage regions. "Chemically modified sites" in this context includes, but is not limited to, the addition of a pattern of chemical functional groups including amino groups, carboxy groups, oxo groups and thiol groups, that can be used to covalently attach nucleases, which may also contain corresponding reactive functional groups; the addition of a pattern of adhesive that can be used to bind the nucleases (either by prior chemical functionalization for the addition of the adhesive or direct addition of the adhesive); the addition of a pattern of charged groups (similar to the chemical functionalities) for the electrostatic attachment of the nucleases, e.g., when the nucleases include charged groups opposite to the sites; the addition of a pattern of chemical functional groups that renders the sites differentially hydrophobic or hydrophilic, such that the addition of similarly hydrophobic or hydrophilic nucleases under suitable conditions will result in association of the nuclease to the sites on the basis of hydroaffinity. In an example, a nuclease may be directly coupled to a cleavage region, whereas in another example nucleases may be attached to intermediary vehicles for attachment, such as microbeads, and such intermediary attached to cleavage regions of the substrate. Beads need not be spherical; irregular particles may be used. In addition, beads may be porous, thus increasing the surface area of the bead available for either capture probe attachment or tag attachment. The bead sizes range from nanometers, e.g., 100 nm, to millimeters, e.g., 1 mm, with beads from about 0.2 µm to about 200 µm being preferred, and from about 0.5 to about 5 µm being particularly preferred, although in one example smaller beads may be used. Examples disclosed herein of attachment of a nuclease to a cleavage region include examples of attaching a nuclease to an intermediary and attachment of an intermediary attached to a nuclease to a cleavage region. Examples of attachment of a nuclease to a substrate can also refer to examples of attaching a nuclease to an intermediary, or attachment of an intermediary to a substrate.

In an example, a nuclease may include an affinity ligand receptor which binds an affinity ligand coupled to a substrate. Attachment of the affinity ligand receptors may be through covalent means, although even relatively weak interactions (e.g., non-covalent) can be sufficient to attach an affinity ligand receptor to a surface, if there are multiple sites of attachment per each affinity ligand receptor. Thus, for example, electrostatic interactions can be used for attachment, for example by having a nuclease or intermediary carrying a charge opposite to the cleavage region. Alternatively, chemical crosslinking may be done.

In an example, the substrate with the bound affinity ligand receptors may be treated (e.g., subject to denaturing or heated conditions) that disrupt the affinity-ligand/affinity-ligand receptor complex to free the bound nucleic acid-affinity ligand complex before, after, or contemporaneously with the cleavage step. The substrate may be washed, dried, prepared, or otherwise treated to be reused in the methods described herein.

In an example, the at least substantially uniform nucleic acid fragments may be collected by washing, dilution, removal, elution, or centrifugation. The substantially uniform nucleic acid fragments may be washed, precipitated, lyophilized, sequenced, sub-cloned, amplified, gel purified, frozen, or stored. In another example, the substantially uniform nucleic acid fragments linearly stretched on the substrate can be sequenced or visualized via fluoresce in situ on the substrate.

In an example, by using a different modification (e.g., treatment) of the substrate, the extent and nature of the interactions of the nucleic acid with the substrate can be altered. In one example, an affinity ligand (e.g., biotin) bound to one end of the nucleic acid in combination with an affinity ligand receptor bound to the modified region of the substrate (e.g., modified region of the substrate coated with streptavidin) provides another means to attach the end of the nucleic acid to the surface. When the nucleic acid is only attached to the glass at a few positions, overstretching of the nucleic acid is avoided.

In an example, a nucleic acid molecule may include an affinity ligand that binds an affinity ligand receptor under the appropriate conditions. An affinity ligand may be attached at an end of the nucleic acid molecule, for example. The affinity ligand may be covalently or non-covalently attached to the nucleic acid molecule.

Alternatively, the nucleic acid molecule may include a nucleotide analog and the affinity ligand is attached to the nucleotide analog. The attached affinity ligand allows for the nucleic acid molecule to be contacted with a substrate including an affinity ligand receptor that binds the affinity ligand, thus binding the nucleic acid molecule to the substrate. A nucleic acid molecule (including an affinity ligand)-sample complex (hybrid) may be contacted with a substrate including an affinity ligand receptor which binds the nucleic acid molecule-sample complex.

Affinity ligands may be incorporated into a target nucleic acid by use of affinity ligand bearing nucleotides and/or primers in an amplification reaction that is used to produce the target nucleic acid in the methods for generating substantially uniform nucleic acid fragments that are set forth herein. Similar methods can be used to introduce affinity ligands into any nucleic acid useful in the methods set forth herein. Examples of amplification reactions include, but are not limited to polymerase chain reaction, random primer amplification, rolling circle amplification and other methods. Affinity ligands can be introduced by photochemical linkage or other chemical techniques as well.

Affinity ligands and affinity ligand receptors are a pair of moieties that bind to each other through covalent or non-covalent interactions. Examples of affinity ligand-affinity ligand receptor partner moieties include but are not limited to biotin-streptavidin, biotin-avidin, receptor-ligand pairs, heterodimerization motif pairs (e.g., complementary leucine zipper motifs, complementary helix-loop-helix motifs), antigen-antibody interactions, polyhistidine (e.g., 6HIS Tag), digoxygenin tags, aptamer-ligand interactions, or multicomponent chemical reactions. Further examples of affinity ligand receptors that bind biotin include but are not limited to avidin, streptavidin (SA), neutravidin, a fragment of SA, a fragment of avidin, and a fragment of neutravidin. In an example, the partner moieties are biotin as the affinity ligand with avidin, neutravidin, or streptavidin as the affinity ligand receptor.

In an example, the nucleic acid molecule may be biotinylated (for example using enzymatic incorporate of biotinylated nucleotides, or photoactivated cross-linking of biotin). Biotinylated nucleic acid molecules can then be captured on a streptavidin-coated surface. Similarly, other hapten-receptor combinations can be used, such as digoxigenin and anti-digoxigenin antibodies. Alternatively, chemical groups can be added in the form of derivatized nucleotides that can then be used to add the nucleic acid molecule to a surface.

Attachments may be covalent, although even relatively weak interactions (e.g., non-covalent) can be sufficient to attach a nucleic acid to a surface, if there are multiple sites of attachment per each nucleic acid. Thus, for example, electrostatic interactions can be used for attachment, for example by having beads carrying a charge opposite to the bioactive agent.

Suitable biotin reagents for attaching biotin to a support surface or a support coupler include amine-reactive biotin labeling reagents include but are not limited to sulfo-NHS-biotin, sulfo-NHS-LC-biotin, sulfo-NHS-LC-LC-biotin, sulfo-NHS-SS-biotin, NHS-PEO$_4$-biotin, NHS-biotin, NHS-LC-biotin, NHS-LC-LC-biotin, PFP-biotin, TFP-PEO-biotin, NHS-iminobiotin trifluoroacetamide, sulfhydryl-reactive biotin labeling reagents (e.g., maleimide-PEO$_2$-biotin, biotin-BMCC, PEO-Iodoacetyl biotin, iodoacetyl-LC-biotin, or biotin-HPDP); carboxyl-reactive biotin labeling reagents (e.g., biotin PEO-amine or biotin PEO-LC-amine); carbohydrate-reactive biotin labeling reagents (e.g., biocytin hydrazide, biotin hydrazide, or biotin-LC-hydrazide); and photoreactive biotin labeling reagents (e.g., psoralen-PEO-biotin). In an example, an affinity ligand may include biotin and be attached to the substrate or substrate coupler using the amine reactive biotin labeling reagent sulfo-NHS-LC-biotin.

Methods similar to those set forth above for attaching affinity ligands, can be used to attach chemically reactive moieties to nucleases or nucleic acids and to solid support surface, such as with thiols, amines, or carboxyls. Accordingly, surface chemistries may be used to facilitate the attachment of the desired functionality. Some examples of these surface chemistries for may include, but are not limited to, amino groups including aliphatic and aromatic amines, carboxylic acids, aldehydes, amides, chloromethyl groups, hydrazide, hydroxyl groups, sulfonates, and sulfates. Moieties can be added to nucleic acids or enzymes that are reactive with such surface functionalizations. The moieties can be added, for example, by chemical modification of nucleic acids or by incorporation of modified primers and/or nucleotides into the amplicon products of an amplification reaction.

Samples including populations of polynucleotides for use in the methods described herein include, but are not limited to, a portion of a gene, a regulatory sequence, genomic DNA, cDNA, and RNA including mRNA and rRNA. The sample may be any length. Complementary target sequence may take many forms. For example, it may be contained within a larger nucleic acid sequence (e.g., all or part of a gene or mRNA, a restriction fragment of a plasmid or genomic DNA, vector). In some examples, a sample used in a method is a genome isolated from one or more cells. The sample can be an amplified product obtained from a genome such as the product of a representational amplification method or whole genome amplification method.

In an example, a sample may be a library of clonal nucleic acids, including DNA and RNA. Individual nucleic acids may be prepared, generally using methods including, but not limited to, propagation in plasmid or phage vectors, amplification techniques including PCR. Nucleic acid libraries may be prepared or may be obtained commercially (Life Technologies, Carlsbad, Calif.). Nucleic acid libraries for use in accordance with the present disclosure may include those including populations of single-stranded or double-stranded nucleic acid molecules, or preferably populations of single-stranded or double-stranded DNA molecules. Other nucleic acid libraries to be normalized in accordance with the present disclosure include those including complementary DNA (cDNA) libraries. cDNA libraries (double stranded or single stranded) can be made using messenger RNA or polyA+ RNA or may be obtained commercially, for example from Life Technologies (Carlsbad, Calif.), or other commercial sources. cDNA libraries used in accordance with the present disclosure are preferably made with reverse transcriptases having substantially reduced RNase H activity. cDNA libraries are housed in vectors that include, but are not limited to, plasmids, cosmids, and phages. Nucleic acid libraries as described herein can be used as samples in the method described herein.

Nucleic acid samples (including nucleic acid libraries) may be prepared from populations of nucleic acid molecules obtained from natural sources that include, but are not limited to organdies, cells, tissues, organs, or organisms. Cells that may be used as sources of nucleic acid molecules may be prokaryotic (bacterial cells, e.g., *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium,* and *Streptomyces* genera); archeaon, such as crenarchaeota, nanoarchaeota or euryarchaeotia; or eukaryotic such as fungi, (e.g., yeasts), plants, protozoans and other parasites, and animals (including insects (e.g., *Drosophila* spp.), nematodes (e.g., *Caenorhabditis elegans*), and mammals (e.g., rat, guinea pig, horse, tapir, cow, sheep, goat, mouse, monkey, non-human primate and human)).

Mammalian somatic cells that may be used as sources of samples (including libraries) of nucleic acids include blood cells (e.g., reticulocytes and leukocytes), endothelial cells, epithelial cells, neuronal cells (e.g., from the central or peripheral nervous systems), muscle cells (e.g., myocytes and myoblasts from skeletal, smooth or cardiac muscle), connective tissue cells (e.g., fibroblasts, adipocytes, chondrocytes, chondroblasts, osteocytes and osteoblasts) and other stromal cells (e.g., macrophages, dendritic cells, Schwann cells). Mammalian germ cells (e.g., spermatocytes and oocytes) may also be used as sources of nucleic acids or libraries for use in accordance with the present disclosure, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, spinal cord, genitourinary, circulatory, lymphoid, gastrointestinal and connective tissue sources, as well as those derived from a mammalian (e.g., mouse, rat, hamster, horse, cow, sheep, goat, pig, monkey, human) embryo, or fetus.

Any of the above prokaryotic or eukaryotic cells, tissues and organs may be normal, diseased, transformed, established, progenitors, precursors, fetal or embryonic. Diseased cells include those involved in infectious diseases (caused by bacteria, fungi or yeast, viruses, or parasites), in genetic or biochemical pathologies (e.g., cystic fibrosis, hemophilia, Alzheimer's disease, Huntington's disease, Parkinson's Disease, muscular dystrophy or multiple sclerosis) or in cancerous processes. Transformed or established animal cell lines (e.g., 293-T cells, 3T3 cells, 721 cells, 9L cells, A172 cells, A20 cells, A253 cells, A2780 cells, A431 cells, A-549 cells, ALC cells, B16 cells, B35 cells, Bas8 cells, BCP-1 cells, BHK cells, BHK-21 cells, BR 293 cells, BxPC3 cells, C3H-10T1/2 cells, C6 cells, C6/36 cells, Cal-27 cells, CHL-60 cells, CHO cells, CMLT1 cells, CMT cells, COR-L23 cells, COS cells, CT26 cells, D17 cells, DH82 cells, DU145 cells, EL4 cells, EM2 cells, EM3 cells, F9 cells, FM3 cells, H1299 cells, H69 cells, HB54 cells, HB55 cells, HCA2 cells, HEK-293 cells, HeLa cells, Hepalcic7 cells, HepG2 cells, HMEC cells, HT-29 cells, Jurkat cells, JY cells, K562 cells, KCL22 cells, KG1 cells, Ku812 cells, KYO1 cells, Lncap cells, MC-38 cells, MCF-10A cells, MCF-7 cells, MDA-231 cells, MDA-468 cells, MDA-MB-438 cells, MDCK II cells, N6 cells, NALM-1 cells, NIH-3T3 cells, NW-145 cells, PC3 cells, PC12 cells, RenCa cells, Saos-2 cells, Sf9 cells, Sf21 cells, SHSY5Y cells, T47D cells, T84 cells, THP-1 cells, U373 cells, U87 cells, U937 cells, VERO cells, WM39 cells, X63 cells, YAC-1 cells, YAR cells) can be used as the source of nucleic acid sample material for use in the accordance with the present disclosure. Other cells, cell lines, tissues, organs and organisms suitable as sources of nucleic acids for use in accordance with the present disclosure will be apparent to one of ordinary skill in the art. These cells, tissues, organs and organisms may be obtained from their natural sources, or may be obtained commercially from sources such as American Type Culture Collection (Rockville, Md.) and others that are known in the art.

Once the starting cells, tissues, organs or other samples are obtained, nucleic acid molecules (e.g., mRNA or poly A+ RNA) can be isolated, and nucleic acid libraries (e.g., cDNA libraries) prepared therefrom. Nucleic acid libraries prepared in such a manner may contain a vast range of abundances of member nucleic acid molecules, depending upon the cell, tissue or organism source, and the stage of development or cell cycle of the source.

A sample useful in the methods set forth herein, can be an isolated genome from a cell or organism such as one of those set forth above. A genome useful in the methods can be a substantially complete genome or fraction thereof. For example, the sample can include a complexity of at least 80%, 90%, 95%, 99% or 99.9% of an organism's genome. Less complex samples can be used as well including for example, a sample having no more than 50%, 40%, 30%, 20% 10%, 5% or 1% of an organism's genome.

A sample useful in the methods described herein can be a nucleic acid library including but not limited to a genomic DNA library, cDNA library, eukaryotic DNA library, Achaean DNA library, or prokaryotic DNA library. The DNA library can have a complexity of at least about 0.5 Gbases, 1 Gbases, 2 Gbases, 3 Gbases, 4 Gbases, 5 Gbases, 10 Gbases or more. A sample useful in the methods described herein can be a genome, transcriptome, or metagenome.

Nucleic acid fragments produced by the methods as described herein include at least two nucleotides. In particular examples, the nucleic acid fragments can be at least about 10, about 25, about 50, about 100, about 150, about 200, about 250, about 300, about 350, about 400, about 450, about 500, about 550, about 600, about 650, about 700, about 750, about 800, about 850, about 900, about 950, about 1,000, about 1,100, about 1,200, about 1,300, about 1,400, about 1,500, about 1,600, about 1,700, about 1,800, about 1,900, about 2,000, about 2,500, about 3,000, about 3,500, about 4,000, about 4,5000, about 5,000, about 5,500, about 6,000, about 6,500, about 7,000, about 7,500, about 8,000, about 8,500, about 9,000, about 10,500, about 11,000, about 12,000, about 13,000, about 14,000, about 15,000, about 16,000, about 17,000, about 18,000, about 19,000, about or 20,000 bases. Alternatively or additionally, the nucleic acid fragments (e.g., oligonucleotides) can be of a length that is no more than 20,000, about 19,000, about 18,000, about 17,000, about 16,000, about 15,000, about 14,000, about 13,000, about 12,000, about 11,000, about 10,000, about 9,500, about 9,000, about 8,500, about 8,000, about 7,500, about 7,000, about 6,500, about 6,000, about 5,500, about 5,000, about 4,500, about 4,000, about 3,500, about 3,000, about 2,500, about 2,000, about 1,900, about 1,800, about 1,700, about 1,600, about 1,500, about 1,400, about 1,300, about 1,200, about 1,100, about 1,000, about 900, about 800, about 700, about 600, about 500, about 400, about 300, about 200, about 150, about 100, about 75, about 50, about 25 or about 10 nucleotides (e.g., base pairs) or shorter. In another example, the nucleic acid fragments can be at least about 1, about 2, about 3, about 4, about 5, about 6, about 7, about 8, about 9, or about 10 kb, as well as about 10, about 11, about 12, about 13, about 14, about 15, about 16, about 17, about 18, about 19, or about 20 kb, as well as about 10, about 20, about 25, about 30, about 35, about 40, about 45, about 50, about 55, about 60, about 65, about 70, about 75, about 80, about 85, about 90, about 95 or about 100 kb as well as about 100, about 200, about 300, about 400, about 500, about 600, about 700, about 800, about 900, about or 1,000 Kb and all increments therein.

In some examples, the nucleic acid fragments may be at least about 1, about 2, about 3, about 4, about 5, about 6, about 7, about 8, about 9, about 10, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 200, about 300, about 400, about 500, about 600, about 700, about 800, about 900, or about 1,000 bases in length.

The nucleic acid fragments may be at least about 1, about 2, about 3, about 4, about 5, about 6, about 7, about 8, about 9, about 10, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 200, about 300, about 400, about 500, about 600, about 700, about 800, about 900, or about 1,000 kb in length. In some examples, the nucleic acid fragments can be about at least 10, about 20, about 30, about 40, about 50, about 60, about 70, about 80, about 90 about or 100 kb in length.

In an example, the nucleic acid fragments can be from at least about 10 to 20, about 10 to 30, about 10 to 40, about 10 to 50, about 10 to 60, about 10 to 70, about 10 to 80, about 10 to 90, or about 10 to 100 bases in length. In a further example, the nucleic acid fragments can be at least about 100 to 200, about 100 to 300, about 100 to 400, about 100 to 500, about 100 to 600, about 100 to 700, about 100 to 800, about 100 to 900, or about 100 to 1,000 bases in length. Alternatively, the nucleic acid fragments can be at least about 10 to 20, about to 30, about 10 to 40, about 10 to 50, about 10 to 60, about 10 to 70, about 10 to 80, about 10 to 90, or about 10 to 100 kb. In a further example, the nucleic acid fragments can be at least about 100 to 200, about 100 to 300, about 100 to 400, about 100 to 500, about 100 to 600, about 100 to 700, about 100 to 800, about 100 to 900, or about 100 to 1,000 kb.

Nucleic acid fragments produced by the methods as described herein may be single stranded or double stranded, as specified, or contain portions of both double stranded and single stranded sequence. The nucleic acid fragments may be DNA, both genomic and cDNA, RNA or a hybrid, where the nucleic acid fragments include any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole.

Predetermined polynucleotide fragment lengths of a suitably consistent length distribution may be produced by patterning cleavage regions on a substrate that are of known, consistent distances from each other. A cleavage region may create a cleavage point within a polynucleotide, creating two ends at the cleavage point (i.e., site of the polynucleotide at which a nuclease within a cleavage region cleaves the polynucleotide). When a target polynucleotide is stretched across the substrate, it would be cleaved at cleavage regions, leaving fragments approximating an inter-cleavage region distance in length. A target polynucleotide may be cleaved at more than one site within a given cleavage region. That is, multiple cleavage points may be created in a given cleavage region, resulting in fragments whose length approximates inter-nuclease distances within a cleavage regions, as well as fragments whose length approximates inter-cleavage region distances. The result may be fragments that roughly fall within two categories, longer fragments (with ends resulting from cleavage points that were in difference cleavage regions from each other) and shorter fragments (with ends from cleavage points that were in the same cleavage region as each other). A distance between cleavage regions may be chosen that is suitably longer than distances between nucleases within individual cleavage regions such that method for separating populations of nucleotide fragments based on disparate sizes allows enriching for the fragments (e.g., those with lengths approximating inter-cleavage region distances) and those to be discarded (e.g., those with lengths approximating distances between nucleases within a cleavage region).

An example includes tagmentation, and a transposase at a cleavage region may cleave a polynucleotide at a cleavage point and add an adapter to each end of the polynucleotide created at the cleavage point. For example, an adapter may be added to the cleaved end of each strand of a double-stranded polynucleotide cleaved at a cleavage point. In some examples, a double-stranded adapter within a transposome may include strands that are not covalently connected to each other (e.g., an adapter including separate polynucleotide strands) and may be added to a double-stranded end created at a cleavage point when a polynucleotide is cleaved by the transposome. In another example, a double-stranded adapter within a transposome may include strands what are covalently connected to each other (e.g., an adapter including the two ends of a polynucleotide strands) and may be added to a double-stranded end created at a cleavage point when a polynucleotide is cleaved by the transposome. The latter example may include adding hairpin loops to ends created at a cleavage point. A double-stranded polynucleotide cleaved at two cleavage regions and having a hairpin loop added to the cleaved strand ends at each cleaved end my form a dumbbell-shaped polynucleotide.

In some examples it may be advantageous to produce fragments of polynucleotides having asymmetrical ends. Asymmetrical in this case means opposing ends (i.e., ends from two different cleavage points) with adapters that differ from each other (e.g., transposomes of two types of cleavage regions do not include adapters that are the same as each other). In accordance with the present disclosure, asymmetrical ends may be produced by cleavage regions on a substrate in a pattern that alternates between two different types of cleavage regions. For example, a first type of cleavage region may have transposomes with nucleic acid-based adapters of a first type, meaning adapters including polynucleotides (e.g., oligonucleotides) of a first nucleotide sequence. A second type of cleavage region may have transposomes with nucleic acid-based adapters of a second type, meaning adapters including polynucleotides (e.g., oligonucleotides) of a second nucleotide sequence.

In this example, the first type of cleavage region does not include the second type of adapters, and the second type of cleavage region does not include the first type of adapters. When polynucleotides are stretched across such a substrate, some fragments will be created with opposite ends that were created by cleavage points at two different types of cleavage regions, e.g. a first type of cleavage region creating one end of the fragment and a second type of cleavage region creating the other end of the fragment. Accordingly, one end of such a fragment includes a first type of adapter and the other end of the fragment includes a second type of adapter. Such fragments have asymmetrical ends. In an example, one type of cleavage region may include adapters that are attached to each other (such as in the form of a hairpin loop), whereas another type of cleavage region may include adapters that are not connected to each other. In such an example, alternating between each type of cleavage region on a surface may result in a double-stranded polynucleotide fragment with a hairpin loop connecting the strands to each other at one end. In another example, both types of cleavage regions may include adapters that are connected to each other. In such an example, alternating between each type of cleavage region on a surface may result in a double-stranded polynucleotide fragment with a hairpin loop connecting the strands to each other at both opposing ends, forming a dumbbell shape.

Some fragments may be created when two cleavage points occur in the same cleavage region. Such fragments may be shorter than the asymmetrical fragments created when cleavage points are from different types of cleavage regions. Further, fragments created when both cleavage points are within the same cleavage region would have symmetrical ends not asymmetrical ends. That is, because both cleavage points would come from the same type of cleavage region as each other (i.e., the same cleavage region), they would have the same adapter types as each other. Separating such fragments from each other may be done by separating them on the basis of size, for example when the distance between cleavage regions is larger than the distance between nucleases within cleavage regions. In another example, fragments with symmetrical ends could be separated from fragments with asymmetrical ends, and the result may include separating longer fragments from shorter fragments. For example, fragments with a first type of adapter could be selected though hybridization selection or affinity binding that selects for a first type of adapter relative to a second type of adapter. This would select for fragments with asymmetrical ends and fragments with symmetrical ends having a first type of adapter at both ends, and not select for fragments that have asymmetrical ends having a second type of adapter at each end. Subsequently, of the fragments thus selected, a subset of fragments could be further selected that include adapters of a second type, though hybridization selection or affinity binding that selects for a second type of adapter relative to a first type of adapter. This would select for fragments with asymmetrical ends and not fragments with symmetrical ends having a first type of adapter at both ends. Insofar as fragments with asymmetrical ends are longer than fragments with symmetrical ends, such a separation method would separate longer fragments from shorter fragments.

Cleavage regions may be any distance from each other, or have any desired pitch, on a substrate. Cleavage region pitch on a surface may be selected to create fragments within a desired range of length. Pitch may be selected to produce a population of fragments with an approximate length based on the fact that a polynucleotide of 20,000 nucleotides is approximately 6 microns in length. The pitch may be about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1 micron, about 1.5 microns, about 2 microns, about 2.5 microns, about 3 microns, about 3.5 microns, about 4 microns, about 4.5 microns, about 5 microns, about 5.5 microns, about 6 microns, about 6.5 microns, about 7 microns, about 7.5 microns, about 8 microns, about 8.5 microns, about 9 microns, about 9.5 microns, about 10 microns, about 11 microns, about 12 microns, about 13 microns, about 14 microns, about 15 microns, about 16 microns, about 17 microns, about 18 microns, about 19 microns, about 20 microns, about 22.5 microns, about 25 microns, about 27.5 microns, or about 30 microns, or within any range therebetween. The pitch may be less than 100 nm or more than 30 microns. Any pitch may be selected that would produce fragments of any of the lengths recited in preceding paragraphs of this disclosure and all such pitches are explicitly contemplated and included herein.

A dimension of a cleavage region may be of any desired size. A dimension across a cleavage region may be about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 about 100 nm, or greater.

In some examples, cleavage regions may be generally coplanar with substrate surface that is not cleavage region. For example, cleavage regions may be patterned on a generally flat substrate surface. In other examples, a substrate may be patterned such that it includes surface that are not all generally coplanar with each other. For example, a substrate surface may have depressions, or elevations, of certain features relative to others. As used herein, the term "depression" refers to a discrete concave feature in a patterned support having a surface opening that is completely surrounded by interstices of the patterned support surface, or separated from other concave features by interstices. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As an example, the depression can be a well, or a trench. Or an elevation may be a column or a post.

In an example, cleavage regions may be surfaces separated from each other by differences in planarity. For example, cleavage regions may be surfaces of depressions such as, for example, trenches or wells, or of any other aforementioned depression, and surfaces of interstices between depressions. Pitch in such case may be determined by depth of the depressions. In another example, cleavage regions may be surfaces of elevations such as, for example, posts or columns or any other feature elevated above the rest of a substrate surface and surfaces of interstices between elevations. Pitch in such case may be determined by height of elevations. Where cleavage regions are surfaces of depressions and surfaces of interstices, or surfaces of elevations and surfaces of interstices, cleavage region type may alternate between depression surface and interstice surface, or between elevation surface and interstice surface. For example, depression surfaces may be of a first cleavage region type, with a first type of transposome including a first type of adapter, and surfaces of interstices between depressions may include a second type of cleavage region, with a second type of transposome including a second type of adapter. In another example, elevation surfaces may be of a first cleavage region type, with a first type of transposome including a first type of adapter, and surfaces of interstices between elevations may include a second type of cleavage region, with a second type of transposome including a second type of adapter. Such patterns of alternating types of cleavage regions may produce fragments with asymmetrical ends. In other examples, cleavage regions on depressions or elevations and interstices therebetween may include transposomes with the same types of adapters as each other and generate fragments with symmetrical ends.

Any suitable method for forming patterns on a substrate, such as to create depressions, elevations, or both, may be used to create such surfaces with differently placed cleavage regions. Photolithography, nanoimprint lithography, etching, or other related methods for microfabrication and nanofabrication of substrate features.

In another example, length of a polynucleotide formed by cleaving a sample polynucleotide may be determined by extending a polynucleotide through a pore of a membrane. One side of the porous membrane may include nucleases such as transposons attached thereto in the vicinity of pore openings. To the opposing side of the membrane, microbeads may be applied to which polynucleotides are attached, through covalent or other attachment as in aforementioned examples of this disclosure. The end of the polynucleotide not attached to the bead may be extended through a pore of the membrane by any suitable method, such as an electrophoretic or other process. The bead to which the end of the polynucleotide is attached may be larger than the pore such that the bead cannot pass through the pore. The orientation of the end of a polynucleotide attached to a bead at one end of a pore through a membrane and its opposite end protruding from the opposing opening of the pore brings the polynucleotide into the vicinity of a nuclease near such pore opening. Cleavage of the polynucleotide near where it extends from an opening of a pore results in a polynucleotide extending from a bead with a length approximate to the thickness of the porous membrane. In an example, transposases attached to the membrane may tagment the polynucleotide, adding an adapter to the end created at the cleavage point near where the polynucleotide exits from a pore. A polynucleotide may subsequently be released from a bead. For example, a polynucleotide may be attached to a bead by an affinity ligand severable by a targeted chemical or enzymatic reaction to release the polynucleotide from the bead. In another example, a copy of the polynucleotide may be synthesized, including an adapter that may have been added in the example of a tagmented polynucleotide. The copy may subsequently be used for intended purposes including sequencing, etc. With multiple polynucleotides attached to bands and extended through pores of such a membrane, a population of polynucleotides of a length approximating the thickness of the membrane may be produced, advantageously having a narrow distribution of sizes.

A membrane may be made from a variant of different materials, including biological membranes (e.g. BLMs (black lipid membranes)), polymer membranes (multiblock copolymers) and solid-state membranes (graphene or inorganic/hybrid materials, silicon membranes, silicon dioxide membranes, silicon nitride (SiNx) membranes), including membranes fabricated using non-lithographic processes (e.g. encapsulated spheres). Pores in a membrane may be made or machined by techniques including chemical etching, Focused Ion Beam (FIB), Focused Electron Beam, lithography (including nanoimprint lithography, multi-layered lithography) and laser-drilling of nanometer scale pores. Beads, such as microbeads (inorganic, organic, polymer particles or hybrid particles) may be as described above in this disclosure. A membrane may be of any thickness intended to attain a population of polynucleotides of a desired length. A porous membrane's thickness may be about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1 micron, about 1.5 microns, about 2 microns, about 2.5 microns, about 3 microns, about 3.5 microns, about 4 microns, about 4.5 microns, about 5 microns, about 5.5 microns, about 6 microns, about 6.5 microns, about 7 microns, about 7.5 microns, about 8 microns, about 8.5 microns, about 9 microns, about 9.5 microns, about 10 microns, about 11 microns, about 12 microns, about 13 microns, about 14 microns, about 15 microns, about 16 microns, about 17 microns, about 18 microns, about 19 microns, about 20 microns, about 22.5 microns, about 25 microns, about 27.5 microns, or about 30 microns, or within any range therebetween. The pitch may be less than 100 nm or more than 30 microns. Any thickness may be selected that would produce fragments of any of the lengths recited in preceding paragraphs of this disclosure and all such thicknesses are explicitly contemplated and included herein.

In an example it may be desirable to maintain nucleases in an enzymatically quiescent state during, for example, combing or other stretching of polynucleotides across a surface so that polynucleotides are not prematurely cleaved, or during extending polynucleotides through a membrane so that a polynucleotide extends fully through a membrane. For example, magnesium and manganese or other ions or factors involved in for nuclease or transposase enzymatic activity may be withheld during stretching or extending until initiation of cleaving of polynucleotides is desired, then added to initiate cleaving once polynucleotides are positioned as desired.

The examples contained herein are offered by way of illustration and are not intended to limit the disclosure.

An example of a substrate including cleavage regions is shown in FIG. 1. A polynucleotide 140 is stretched across a substrate 110. Stretching may be accomplished by molecular combing, with a flow or motion of polynucleotides or buffer including polynucleotides across a substrate surface in the direction indicated by arrow 150. Cleavage regions 120 are separated by gap 130. In this example, cleavage regions 120 are separated from each other by a consistent gap 130 across the substrate.

Figure 2:
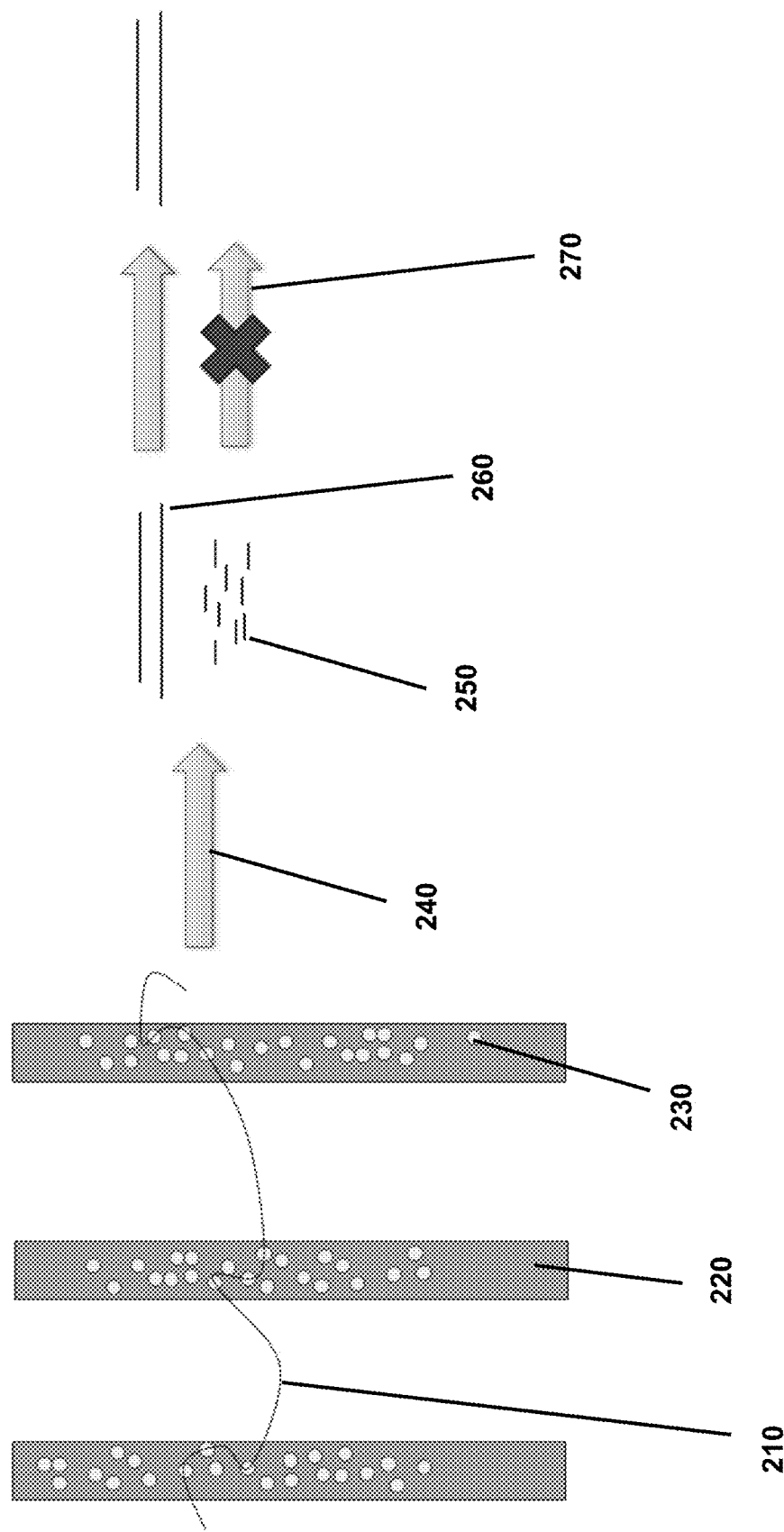
FIG. 2 is an illustration of an example of a polynucleotide cleaved by a plurality of equally spaced cleavage regions including transposases to form a plurality of polynucleotide fragments, and separation of a population of longer polynucleotide fragments from a population of shorter polynucleotide fragments.

FIG. 2 illustrates a close-up of a portion of the substrate illustrated in FIG. 1. Polynucleotide 210 is stretched across cleavage regions 220 of a substrate. Cleavage regions 220 include nucleases 230, such as transposases. Upon initiation of cleaving 240, longer fragments 260 are created, resulting from cleavage of cleavage points of the polynucleotide, and creation of the two cleavage ends, at two different cleavage regions. Shorter fragments 250 may also be created resulting from cleavage of cleavage points of the polynucleotide, and creation of the two cleavage ends, at the same cleavage region. In the example shown in FIG. 2, longer and shorter fragments can be separated from each other and, in this case, longer fragments selected, resulting in a population of polynucleotides enriched for a narrow distribution of lengths.

Figure 3:
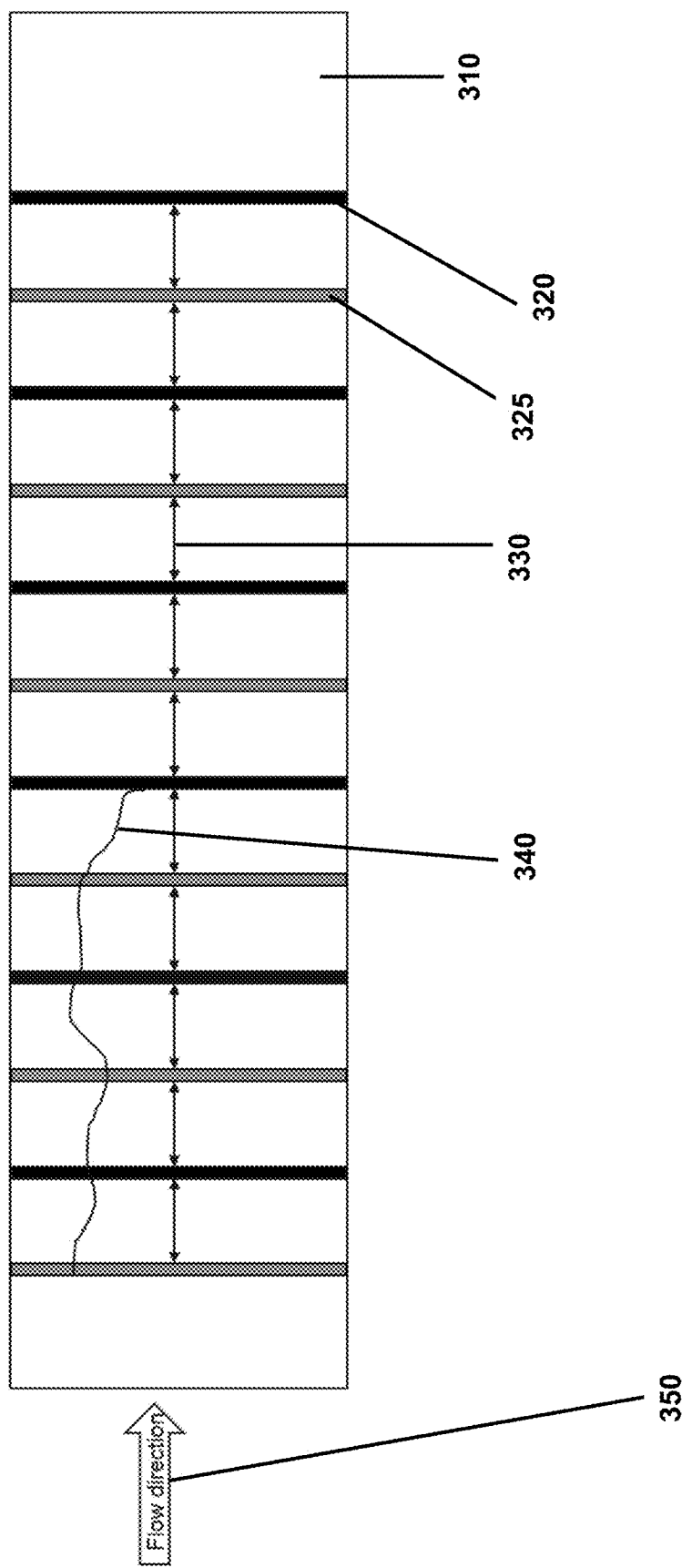
FIG. 3 is an illustration of an example of a polynucleotide stretched over a substrate including a plurality of equally spaced cleavage regions, wherein the cleavage regions include two types of cleavage regions, and the plurality of equally spaced cleavage regions alternate between the two types of cleavage regions.

FIG. 3 shows an example like FIG. 1 but having two different types of cleavage regions. A polynucleotide 340 is stretched across a substrate 310. Stretching may be accomplished by molecular combing, with a flow or motion of polynucleotides or buffer including polynucleotides across a substrate surface in the direction indicated by arrow 350. Cleavage regions are arranged in an alternating pattern between a first type of cleavage region 320 and a second type of cleavage region 325. Cleavage regions 320 and 325 are separated by gap 330. In this example, cleavage regions 320 and 325 are separated from each other by a consistent gap 330 across the substrate.

Figure 4:
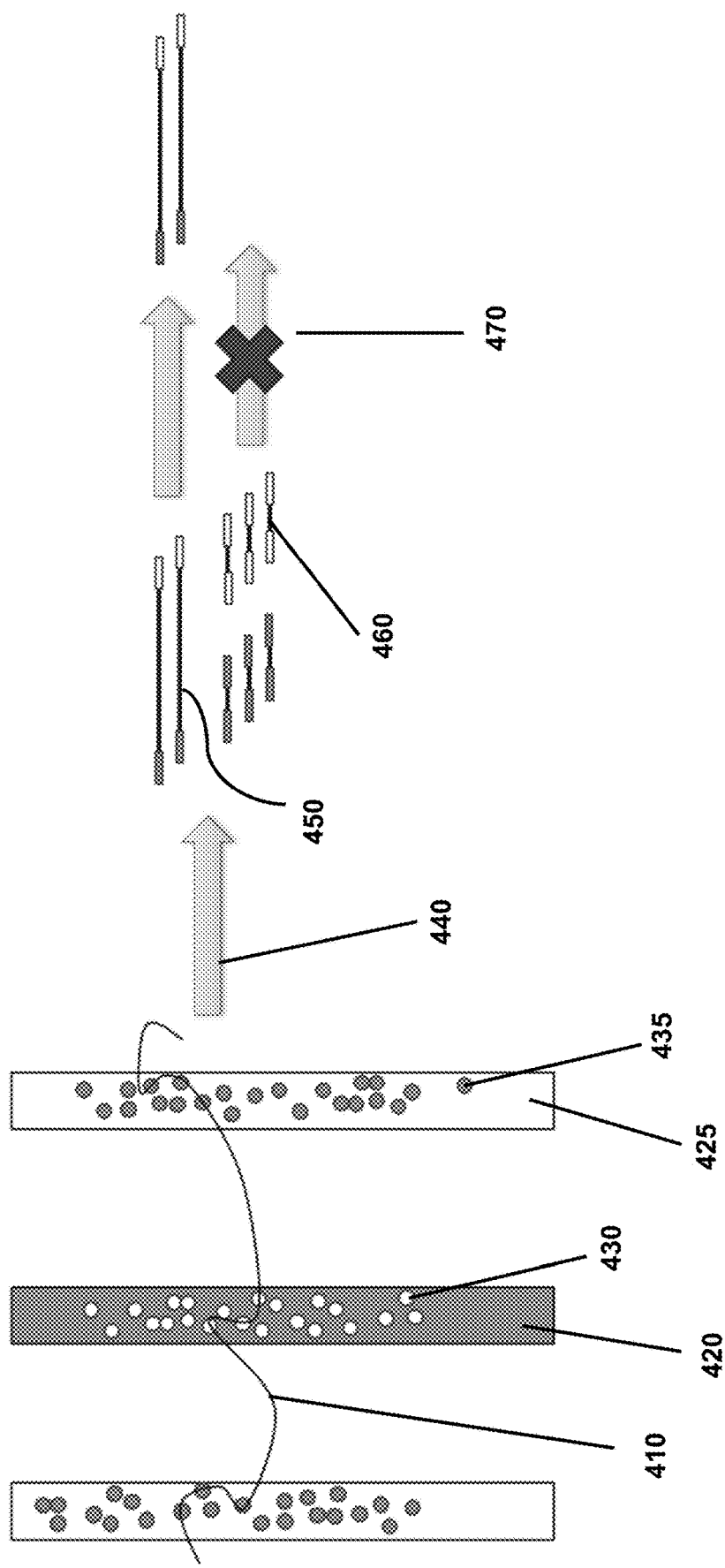
FIG. 4 is an illustration of an example of a polynucleotide cleaved by a plurality of two types of equally spaced cleavage regions including transposases, wherein each type of cleavage region includes a type of nucleic acid-based adapter, and separation of a population of longer polynucleotide fragments from a population of shorter polynucleotide fragments.

FIG. 4 illustrates a close-up of a portion of the substrate illustrated in FIG. 2. Polynucleotide 410 is stretched across cleavage regions 420 and 425 of a substrate. A first type of cleavage region 420 include a first type of nucleases 430, such as transposases. A second type of cleavage region 425 include a second type of nucleases 435, such as transposases. Upon initiation of cleaving 440, longer fragments 150 are created, resulting from cleavage of cleavage points of the polynucleotide, and creation of the two cleavage ends, at two different cleavage regions. Shorter fragments 460 may also be created resulting from cleavage of cleavage points of the polynucleotide, and creation of the two cleavage ends, at the same cleavage region.

In this example, a first type of cleavage region 420 includes a first type of transposon 430 including a first type of adapter. A second type of cleavage region 425 includes a second type of transposon 435 including a second type of adapter. As a result, longer polynucleotides 450 have asymmetrical ends and shorter polynucleotides 460 have symmetrical ends. In the example shown in FIG. 4, longer fragments having asymmetrical ends can be separated from shorter fragments having symmetrical ends and, in this case, longer fragments with asymmetrical ends selected, resulting in a population of polynucleotides enriched for a narrow distribution of lengths and asymmetrical ends.

Figure 5:
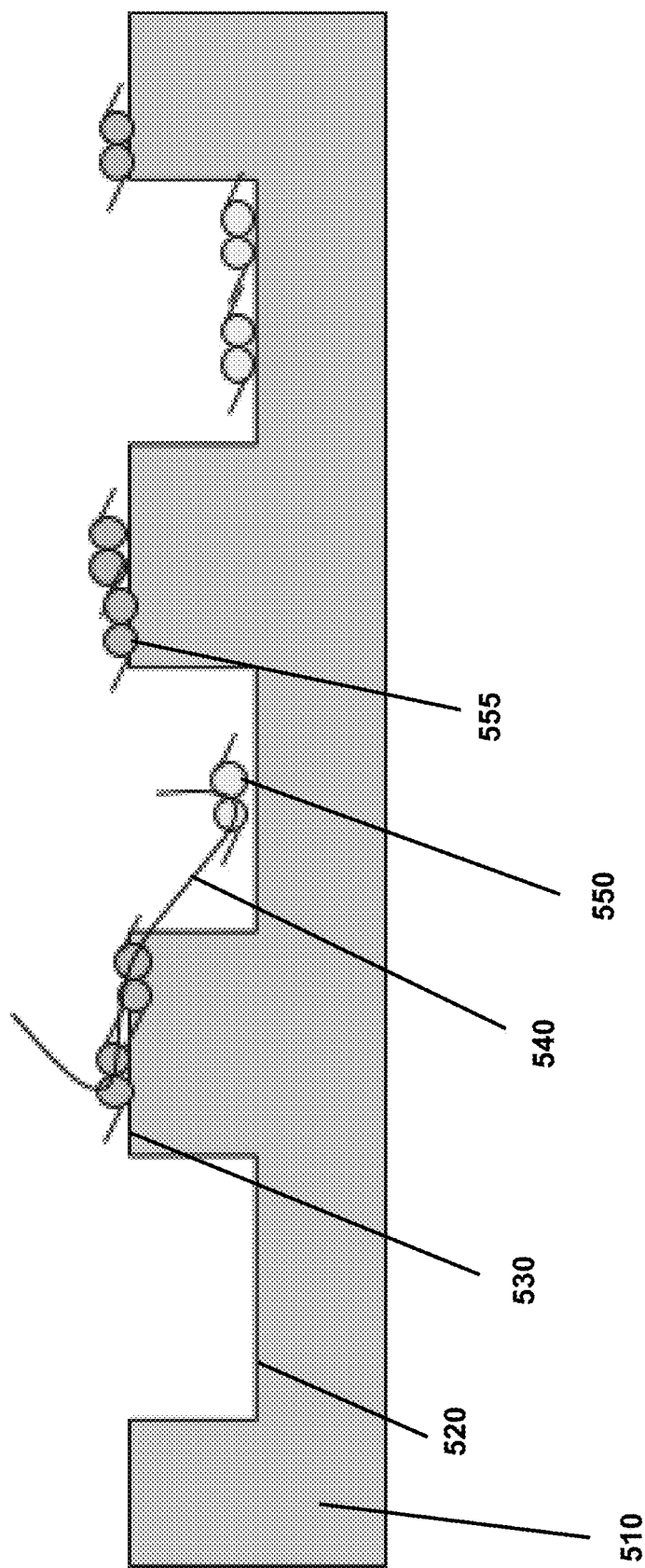
FIG. 5 is an illustration of an example of a substrate including trenches alternating with interstices and cleavage regions including surfaces of the trenches and surfaces of the interstices.

FIG. 5 illustrates an example of a substrate 510 having depressions 520 and interstices 530, comprising different types of cleavage region. Surfaces of depressions 520, in this example trenches, have transposons 550 of a first type including a first type of adapter. Surfaces of interstices 530 have transposons 555 of a second type including a second type of adapter. A polynucleotide 540 stretched over the substrate 510 may be cleaved at each type of cleavage region. Much as in the examples of cleavage regions shown in FIGS. 1 and 2, substrate 510 may yield longer fragments with lengths determined by the depth of depressions 520. Other, shorter fragments may also be created when two ends of a fragment were created by transposons with the same cleavage region. As in FIGS. 2 and 4, longer fragments may be asymmetrical (due to transposons 550 and 555 of different types cleavage regions 530 and 520 creating opposing ends of a fragment). Also as in FIGS. 2 and 4, shorter fragments may be symmetrical (due to both ends of a fragment having been created at the same cleavage region).

Figure 6:
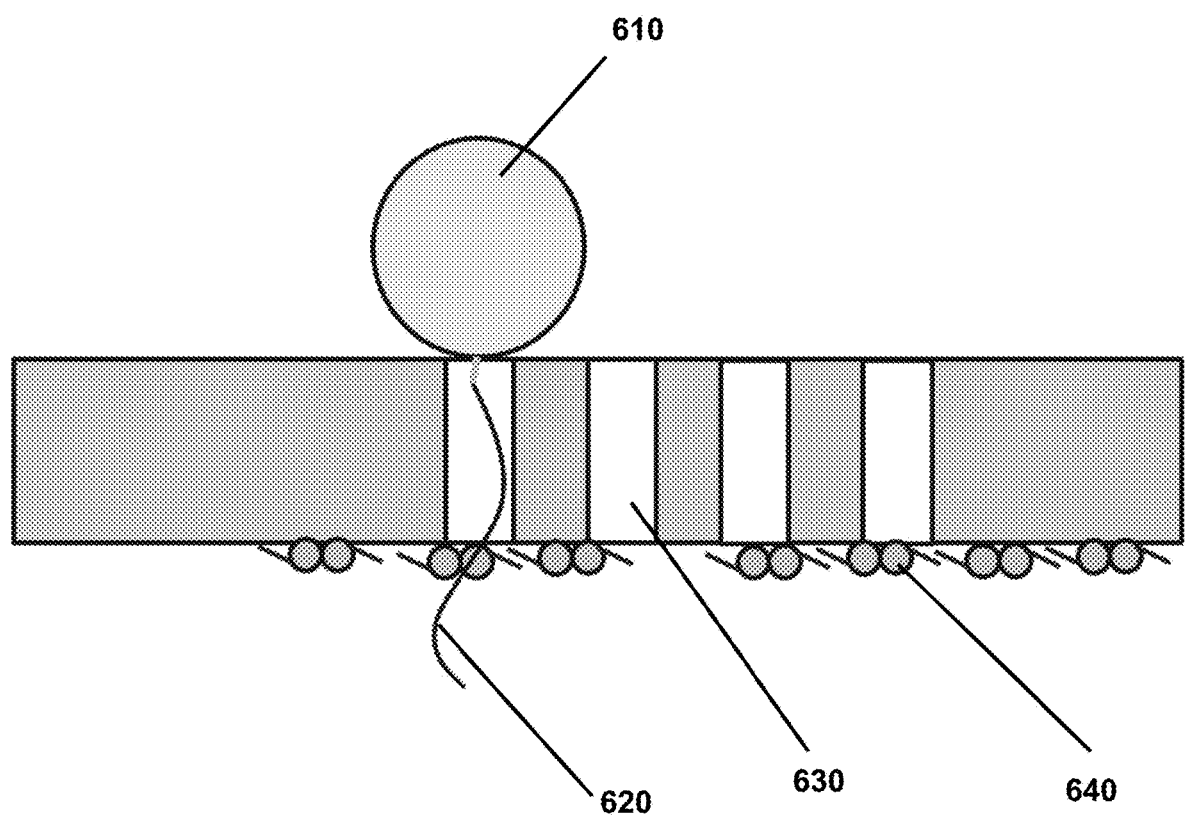
FIG. 6 is an illustration of an example of extending an end of a sample nucleic acid through a pore of a membrane, wherein the sample nucleic acid is attached to a bead, the pore is narrower than the bead, and a side of the membrane opposite the bead includes a nuclease.

FIG. 6 illustrates an example where a polynucleotide 620 attached to a bead 610 is extended through a pore of a membrane 630. Bead 610 is too large to fit through pore 630. Nucleases such as transposases 640 are attached to a surface of the membrane opposing the bead 610 and in proximity to opening of pore 630. Nuclease, such as transposase 640 may cleave the polynucleotide near where it exits the pore. A plurality of polynucleotides 620 attached to beads 610 and extended through such pores 630 and cleaved by such nucleases 640 would result in a population of polynucleotides 620 attached to beads 610 having lengths approximately equal to the thickness of the membrane. Polynucleotides could subsequently be separated from beads or copies synthesized for use in a subsequent process such as a sequencing method. In an example, nucleases such as transposases 640 may tagment the polynucleotides by adding adapters thereto.

Figure 8A:
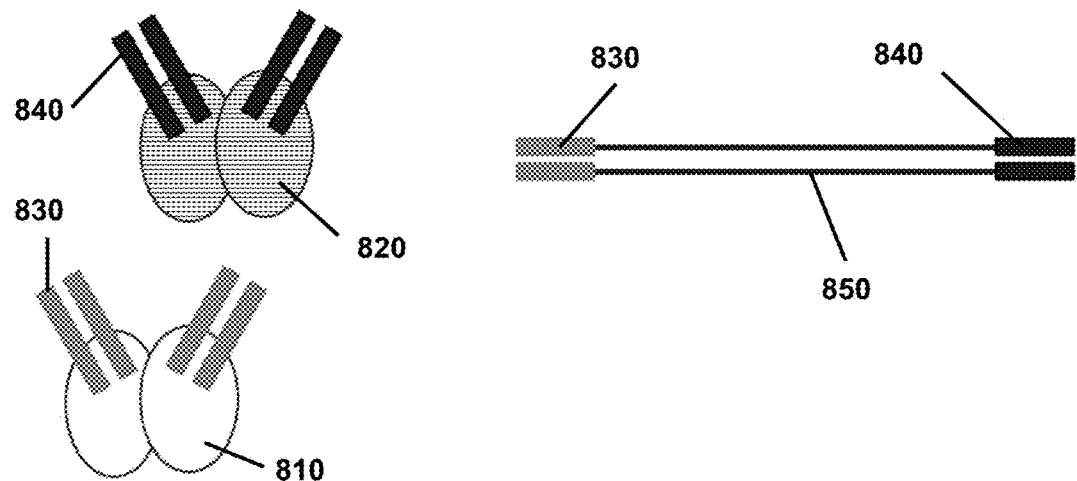
FIG. 8A is an illustration of an example of transposases for cleaving a double-stranded polynucleotide and adding nucleic acid-based adapters to the cleaved end wherein the nucleic acid-based adapters are not connected to each other.
Figure 8B:
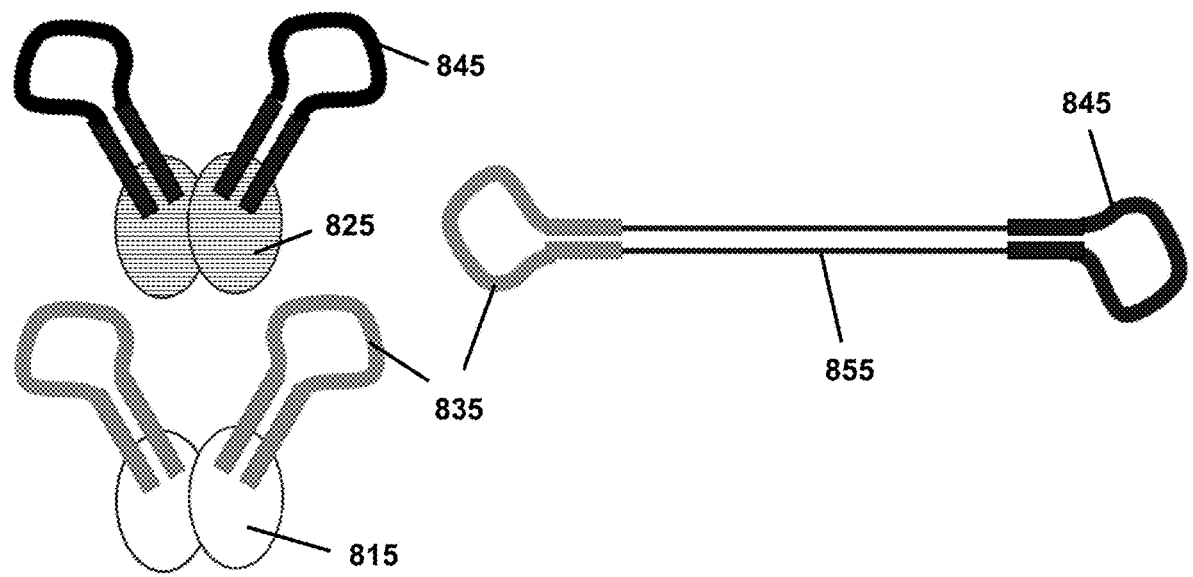
FIG. 8B is an illustration of an example transposases for cleaving a double-stranded polynucleotide and adding nucleic acid-based adapters to the cleaved end wherein the nucleic acid-based adapters are connected to each other.

FIGS. 8A and 8B illustrate examples of adding adapters to ends of a cleaved polynucleotide using transposomes. FIG. 8A relates to an example where two types of transposomes, a first type 810 and a second type 820, attach adapters to ends of a double-stranded polynucleotide. A first type of transposome 810 includes transposases, and also includes a first type of adapters 830. Two first type of adapters 830 are included in the first type of transposome 810. The first type of adapters 830 are not connected to each other. A second type of transposome 820 includes transposases, and also includes a second type of adapters 840. Two second type of adapters 840 are included in the second type of transposome 830. The second type of adapters 840 are not connected to each other. In an example, a first type of transposome 810 may be included in a first type of cleavage region and a second type of transposome 820 may be found in a second type of cleavage region, and a substrate may include cleavage regions that alternate between a first type and a second type, such as is illustrated in FIG. 3 or FIG. 6. A polynucleotide 850 is shown after having been cleaved by a first type of transposome 810 at one end and a second type of transposome 820 at the opposite end. Cleavage of the polynucleotide 850 crates an end including a pair of complementary ends. Cleavage by a transposome also includes adding adapters. A first type of adapter 830 has been added to each strand at the end of the polynucleotide 850 that was cleaved by the first type of transposome 810. A second type of adapter 840 has been added to each strand at the end of the polynucleotide 850 that was cleaved by the second type of transposome 820. The two of the first type of adapters 830 need not be identical or fully complementary to each other and the two of the second type of adapters 840 need not be identical or fully complementary to each other.

FIG. 8B relates to an example where two types of transposomes, a first type 815 and a second type 825, attach adapters to ends of a double-stranded polynucleotide, wherein adapters within a transposome are attached to each other. A first type of transposome 815 includes transposases, and also includes a first type of adapters 835. Two first type of adapters 835 are included in the first type of transposome 815. The first type of adapters 835 are connected to each other in a hairpin loop. A second type of transposome 825 includes transposases, and also includes a second type of adapters 845. Two second type of adapters 845 are included in the second type of transposome 825. The second type of adapters 845 are connected to each other in a hairpin loop. In an example, a first type of transposome 815 may be included in a first type of cleavage region and a second type of transposome 825 may be found in a second type of cleavage region, and a substrate may include cleavage regions that alternate between a first type and a second type, such as is illustrated in FIG. 3 or FIG. 6. A polynucleotide 855 is shown after having been cleaved by a first type of transposome 815 at one end and a second type of transposome 825 at the opposite end. Cleavage of the polynucleotide 855 crates an end including a pair of complementary ends. Cleavage by a transposome also includes adding hairpin loops to ands of the polynucleotide 855. A first type of adapter 835 has been added to each strand at the end of the polynucleotide 855 that was cleaved by the first type of transposome 815, wherein the adapters are connected to each other forming a hairpin loop. A second type of adapter 845 has been added to each strand at the end of the polynucleotide 855 that was cleaved by the second type of transposome 825, wherein the adapters are connected to each other forming a hairpin loop.

Figure 9:
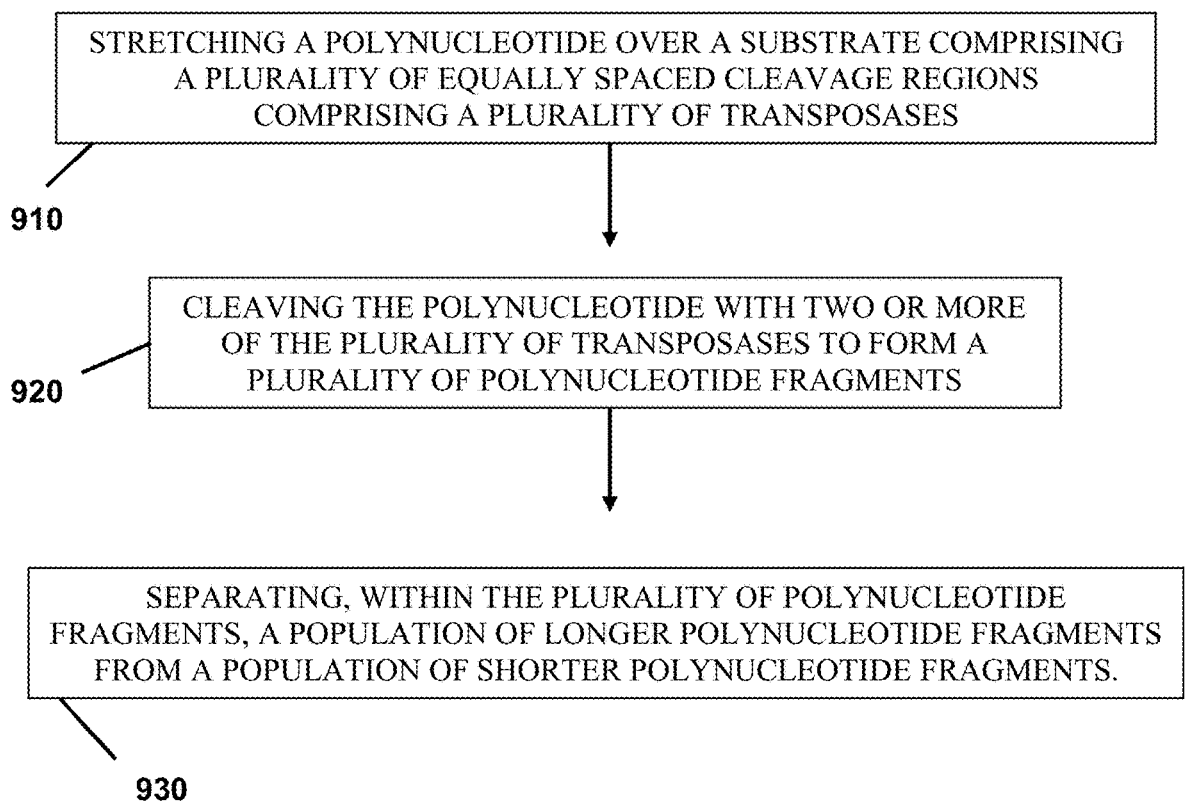
FIG. 9 is a flow chart illustrating a method in accordance with the present disclosure.

FIG. 9 is a flowchart of a method as disclosed herein, in accordance with the foregoing. Shown in 910 is stretching a polynucleotide over a substrate comprising a plurality of equally spaced cleavage regions comprising a plurality of transposases. Stretching may include attaching an end of the polynucleotide to the substrate and extending the polynucleotide across the length of the substrate. For example, molecular combing may be used to stretch the polynucleotide across the substrate, using, for example a fluid flow method or application of weak forces such as electrophoresis or receding meniscus. In an example, molecular combing may include use of a second substrate, in addition to the first substrate across which the polynucleotide is stretched. A fluid including the polynucleotide in solution may be is drawn across the first substrate by the second substrate, causing stretching of the polynucleotide across the first substrate as the fluid is drawn across it by the second substrate. The solution may include a plurality of polynucleotides and some, most, or all of the polynucleotides in the solution may be stretched across the first substrate, such as by molecular combing, which may include use of a second substrate as described. In an example, bi-directional molecular combing may be used. Bi-directional molecular combing may include use of a second substrate and using the second substrate to draw the solution over the first substrate by moving the second substrate in a first direction, then changing the direction in which the second substrate is moved to a second direction. Bi-directional combing may increase the number of polynucleotides included in a solution that are stretched across the first substrate. An example of bi-directional combing is illustrated in FIG. 7.

A substrate over which the polynucleotide is stretched may include a plurality of equally spaced cleavage regions. Cleavage regions may be formed by attaching nucleases such as transposases to a substrate surface, such as a silanized glass or other surface to which nucleases may be attached, covalently or otherwise. Cleavage regions may be equally spaced from each other across the surface, with cleavage regions of a given width separated from each other by a gap between cleavage regions in the surface. Example of a polynucleotide stretched over a substrate comprising a plurality of equally spaced cleavage regions are illustrated in FIGS. 1 and 3 as described above.

Shown at 920 is cleaving the polynucleotide with two or more of the plurality of transposases to form a plurality of polynucleotide fragments. Widths of gaps between cleavage regions may determine lengths of polynucleotide fragments resulting from cleavage of the polynucleotide by transposases in the cleavage regions. For example, a polynucleotide may be stretched across two cleavage regions (if not more). The gap between the two cleavage regions does not include nucleases such as transposases. The polynucleotide will be cleaved by nucleases included in cleavage regions. Thus, a population of polynucleotides will be created by the cleaving whose length is approximately at least the distance of the gap, such fragments being cleaved at one end by a nuclease in one cleavage region and cleaved at the other end by a nuclease in another cleavage region. The polynucleotide may also be cleaved by more than one nuclease within a single cleavage region. Polynucleotide fragments both of whose ends were created by cleavage of the polynucleotide by nucleases within the same cleavage region as each other would be short fragments because of the proximity of such nucleases to each other. Cleavage therefore leads to formation of two populations of polynucleotide fragments, one including longer polynucleotide fragments and one including shorter polynucleotide fragments. Examples of the cleaving forming populations of longer and shorter polynucleotide fragments are illustrated in FIG. 2 (see 250 and 260) and 4 (see 450 and 460).

Shown at 930 is separating, within the plurality of polynucleotide fragments, a population of longer polynucleotide fragments from a population of shorter polynucleotide fragments. Polynucleotide fragments within the population of longer polynucleotide fragments may be separated from polynucleotides within the shorted population of polynucleotides on the basis of, for example, size. For example, gel size selection or another method for separating polynucleotides from each other on the basis of differences in size (such as may differentially impede their motion through a gel or other medium, with shorter polynucleotide fragments traveling faster than larger polynucleotide fragments and thereby being separable based on speed of travel through the medium) may be used. As explained further below, differences in adapters that may be added to ends of polynucleotide fragments during the cleaving may also be used to separate polynucleotides of the population of longer polynucleotide fragments from polynucleotides of the population of shorter polynucleotide fragments. Examples of separating polynucleotide fragments of a population of longer polynucleotide fragments from a population of shorter polynucleotide fragments is illustrated in FIG. 2 (see 270) and 4 (see 470).

In an example, the polynucleotide may be a double-stranded polynucleotide. Cleaving includes creating, with an endonuclease such as a transposase, two pairs of complementary ends, i.e., a pair of complementary ends at each of two sides of the break (or cleavage point) created in the polynucleotide by the cleaving, wherein one pair had been attached to the other before the cleaving. A nuclease such as a transposase may cleave the polynucleotide and create the cleavage point and pairs of complementary ends. The transposase may also add an adapter to each strand of a pair of complementary ends. Examples are illustrated in FIGS. 4 and 8A. In an example, the adapters added to the ends of a complementary pair of ends are not connected to each other, such as illustrated in FIGS. 4 and 8A. In another example, adapters added to the ends of a complementary pair of ends may be connected to each other, such as where the adapters are ends of a hairpin loop. An example is illustrated in FIG. 8B.

In some examples, a substrate may include different types of cleavage regions, such as a first type of cleavage region and a second type of cleavage region. Cleavage regions on the substrate may alternate between the two types of cleavage regions. An example of a substrate with two, alternating types of cleavage regions is illustrated in FIG. 4. In another example, the substrate may include trenches and interstices, or posts and interstices, or wells and interstices, or other patterned features alternating with interstices, and the surfaces of the trenches, posts, wells, etc. may include one type of cleavage region and the surface of the interstices may include another type of cleavage region. An example is shown in FIG. 5.

The two types of cleavage regions may include different types of adapters from each other. For example a first type of cleavage region may include a first type of adapter and a second type of cleavage region may include a second type of adapter. Adapters may be included in complex with a transposase as a transposon. Creation of pairs of complementary ends at a cleavage point by a transposon in a first or second type of cleavage region, including a first or second type of adapter, respectively, may include addition of one type of adapter or another to the pairs of complementary ends formed in the cleavage region (i.e., a first type of adapter or a second type of adapter, respectively).

In such an example, polynucleotide fragments formed by cleavage of a polynucleotide at two different cleavage regions may have a type of adapter at one end of the polynucleotide fragment that differs from the type of adapter at the opposite end of the polynucleotide fragment. Polynucleotide fragments formed by cleavage of a polynucleotide by two transposons in the same cleavage region as each other may have a type of adapter at one end of the polynucleotide fragment that is the same as the type of adapter at the opposite end of the polynucleotide fragment. Polynucleotide fragments with types of adapters at opposing ends that differ from each other and polynucleotide fragments with types of adapters at opposing ends that are the same as each other may be separated from each other on the basis of selection and exclusion for different adapter types.

For example, oligonucleotides complementary or to a nucleotide sequence of one but not the other type of the two types of adapters may be used to separate polynucleotide fragments of different populations from each other. For example, a first type of oligonucleotide may be complementary to a nucleotide sequence of a first type of adapter but not to any sequence of the second type of adapter, and a second type of oligonucleotide may be complementary to a nucleotide sequence of a second type of adapter but not to any sequence of the first type of adapter. Some polynucleotide fragments may have a first type of adapter at one end, to which the first type of oligonucleotide but not the second type of oligonucleotide may be complementary, and a second type of adapter at the opposite end, to which the second type of oligonucleotide but not the first type of oligonucleotide may be complementary. Other polynucleotide fragments may have the first type of adapter at both opposing ends, to which the second type of oligonucleotide is not complementary, and other polynucleotide fragments may have the second type of adapters at both opposing ends, to which the first type of adapter is not complementary. Selection from the combined populations of polynucleotide fragments caused by the cleaving may take advantage of differential complementarity of ends of different populations of polynucleotide fragments.

For example, oligonucleotides of one or another type may be attached to a substrate, such as beads, surfaces of a solid or porous substrate, etc., and the mixed populations of polynucleotide fragments may contact the oligonucleotides. If the populations of polynucleotide fragments contact the first type of oligonucleotides, the population of polynucleotide fragments with the second type of adapters at both ends may not hybridize to the oligonucleotides whereas the other populations of polynucleotide fragments (each of which includes the first type of adapter) may hybridize to the oligonucleotides. Nonhybridized polynucleotide fragments may then be discarded, and hybridized oligonucleotide fragments eluted and collected.

The eluted polynucleotide fragments would include polynucleotide fragments having different types of adapters at opposing ends and polynucleotide fragments have the first type of adapters at each end. These mixed populations could then contact oligonucleotides (e.g., attached to beads, surfaces of a solid or porous substrate, etc.) of the second type. Polynucleotide fragments with adapters of the first type at opposing ends may not hybridize to the second type of oligonucleotide and polynucleotide fragments with a first type of adapter at one end and a second type of adapter an the opposing end may hybridize to the second type of oligonucleotide. Nonhybridized polynucleotide fragments may be discarded and hybridized polynucleotide fragments eluted and selected, resulting in separation of a population of polynucleotides with different types of adapters at opposing ends from populations of polynucleotide fragments with the same type of adapter at opposing ends.

Polynucleotide fragments with different types of adapters at different ends would also be of a population of longer polynucleotide fragments relative to polynucleotide fragments that have adapters at opposing ends that are the same as each other. Polynucleotide fragments with adapter types at opposing ends that differ from each other would have been formed by cleavage at one end by one type of cleavage region and by cleavage at the opposing end by a different type of cleavage region. Separating polynucleotide fragments having adapter types at opposing ends that differ from each other from populations of polynucleotide fragments having adapter types at opposing ends that are the same as each other may therefore also include separating a population of longer polynucleotide fragments from a population of shorter polynucleotide fragments. In an example, size (e.g., gel size selection) and adapter-based selection may both be used, such as if either method of separating populations of polynucleotides does not completely separate populations on its own but in combination does so. An example of separating, within the plurality of polynucleotide fragments, a population of longer polynucleotide fragments from a population of shorter polynucleotide fragments on the basis of whether polynucleotide fragments have adapters at opposing ends that differ from (i.e., longer polynucleotide fragments) or are the same as (i.e., shorter polynucleotide fragments) each other is illustrated in FIG. 4 (see, e.g., 470).

Figure 10:
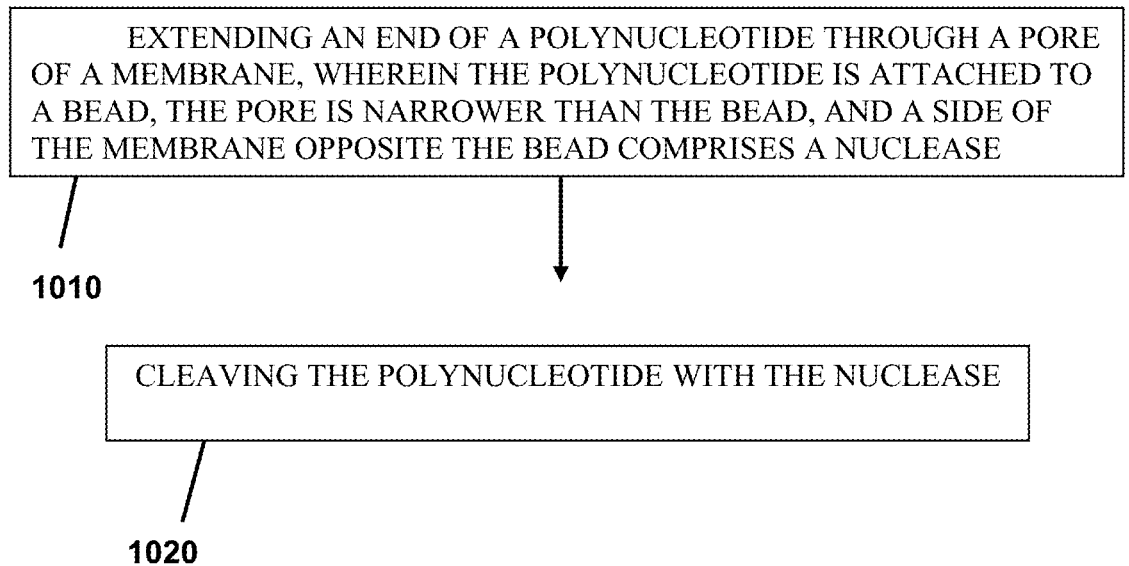
FIG. 10 is a flow chart illustrating a method in accordance with the present disclosure.

FIG. 10 is a flowchart of a method as disclosed herein, in accordance with the foregoing. Shown in 1010 is extending an end of a polynucleotide through a pore of a membrane, wherein the polynucleotide is attached to a bead, the pore is narrower than the bead, and a side of the membrane opposite the bead comprises a nuclease. Extending may include, for example, electrophoresing an end of a polynucleotide through a pore of a membrane. An example is illustrated in FIG. 6, showing a membrane with pores, a polynucleotide attached to a bead that is wider than the pores, and nucleases on the side of the membrane opposite the bead. The polynucleotide may be single stranded or double stranded. Nucleases on the side of the membrane opposite the bead cleave the polynucleotide once it has been extended through the pore, as shown in 1020. In an example, multiple bead-attached polynucleotides may be extended through pores of the membrane, wherein pore size excludes passage of a bead therethrough. Once polynucleotides have extended through the membrane, nucleases on the membrane side opposite the bead may cleave the polynucleotides. Cleavage thereby may create a population of polynucleotides with a size distribution approximating the thickness of the membrane. The population of polynucleotide fragments may then be released from the bead, such as by chemical cleavage of a reversible bioconjugation moiety, peptide linkage, cleavable polynucleotide fragment, or other separable attachment ligand. In another example, a polymerase may make a copy of a strand of a polynucleotide fragment attached to a bead after cleavage. In another example, one strand of a double-stranded polynucleotide fragment may be attached to a bead and the complementary strand may not be attached to the bead, such that the non-attached strand can be dehybridized from the attached strand after the cleavage. Separating a population of polynucleotide fragments with a length approximating the thickness of the membrane may include any of the foregoing examples of collecting or copying polynucleotide fragments after the cleaving.

As in previous examples, nucleases may be transposons including transposases. Transposases may include adapters that are not attached to each other, or adapters that are attached to each other, such as where a pair of adapters include ends of a hairpin loop. Cleaving may include attaching adapters to ends of the polynucleotide fragment created by the cleaving.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein and may be used to achieve the benefits and advantages described herein.

What is claimed is:

1. A method, comprising
stretching a double-stranded polynucleotide over a substrate comprising a plurality of two alternating types of equally spaced cleavage regions comprising a plurality of transposases, wherein a first type of cleavage region comprises a first type of adapter and not a second type of adapter and a second type of cleavage region comprises the second type of adapter and not the first type of adapter,
cleaving the polynucleotide with two or more of the plurality of transposases to form a plurality of polynucleotide fragments comprising two ends, wherein the cleaving comprises adding adapters to both strands of each end, and
separating, within the plurality of polynucleotide fragments, a population of longer polynucleotide fragments from a population of shorter polynucleotide fragments.

2. The method of claim 1, wherein the adapters added to strands of an end are not connected to each other.

3. The method of claim 1, wherein the adapters added to strands of an end are connected to each other.

4. The method of claim 1, wherein the substrate comprises trenches alternating with interstices, and the cleavage regions comprise surfaces of the trenches and surfaces of the interstices.

5. The method of claim 1, wherein the substrate comprises posts alternating with interstices, and the cleavage regions comprise surfaces of the posts and surfaces of the interstices.

6. The method of claim 1, wherein the substrate comprises wells alternating with interstices, and the cleavage regions comprise surfaces of the wells and surfaces of the interstices.

7. The method of claim 3, wherein the adapters comprise a hairpin loop when attached to the strands.

8. The method of claim 1, wherein the stretching comprises bi-directional molecular combing.

9. The method of claim 1, wherein the first type of adapters are not connected to each other.

10. The method of claim 1, wherein the first type of adaptors are connected to each other.

11. The method of claim 10, wherein the first type of adapters comprise a hairpin loop when attached to the strands.

12. The method of claim 1, wherein the second type of adapters are not connected to each other.

13. The method of claim 1, wherein the second type of adapters are connected to each other.

14. The method of claim 13, wherein the second type of adapters comprise a hairpin loop when attached to the strands.

15. A method, comprising
stretching a double-stranded polynucleotide over a substrate comprising a plurality of two alternating types of equally spaced cleavage regions comprising a plurality of transposases, wherein a first type of cleavage region comprises a first type of adapter and not a second type of adapter and a second type of cleavage region comprises the second type of adapter and not the first type of adapter, cleaving the polynucleotide with two or more of the plurality of transposases to form a plurality of polynucleotide fragments comprising two ends, wherein the cleaving comprises adding adapters to strands of each end, wherein the first type of adapters form hairpin loops when attached to the strands and the second type of adapters form hairpin loops when attached to the strands, and separating, within the plurality of polynucleotide fragments, a population of longer polynucleotide fragments from a population of shorter polynucleotide fragments.

16. The method of claim 15, wherein the substrate comprises trenches alternating with interstices, and the cleavage regions comprise surfaces of the trenches and surfaces of the interstices.

17. The method of claim 15, wherein the substrate comprises posts alternating with interstices, and the cleavage regions comprise surfaces of the posts and surfaces of the interstices.

18. The method of claim 15, wherein the substrate comprises wells alternating with interstices, and the cleavage regions comprise surfaces of the wells and surfaces of the interstices.

19. The method of claim 15, wherein the stretching comprises bi-directional molecular combing.

20. A method, comprising stretching a double-stranded polynucleotide over a substrate comprising a plurality of two alternating types of equally spaced cleavage regions comprising a plurality of transposases, wherein a first type of cleavage region comprises a first type of adapter and not a second type of adapter and a second type of cleavage region comprises the second type of adapter and not the first type of adapter, wherein the adapters within cleavage regions are not connected to each other, cleaving the polynucleotide with two or more of the plurality of transposases to form a plurality of polynucleotide fragments comprising two ends, wherein the cleaving comprises adding adapters to strands of each end, separating, within the plurality of polynucleotide fragments, a population of longer polynucleotide fragments from a population of shorter polynucleotide fragments, and the stretching comprises bi-directional molecular combing.

21. The method of claim 20, wherein the substrate comprises trenches alternating with interstices, and the cleavage regions comprise surfaces of the trenches and surfaces of the interstices.

22. The method of claim 20, wherein the substrate comprises posts alternating with interstices, and the cleavage regions comprise surfaces of the posts and surfaces of the interstices.

23. The method of claim 20, wherein the substrate comprises wells alternating with interstices, and the cleavage regions comprise surfaces of the wells and surfaces of the interstices.

* * * * *